US012630557B2

(12) United States Patent
Gong et al.

(10) Patent No.: US 12,630,557 B2
(45) Date of Patent: May 19, 2026

(54) SALT AND CRYSTAL FORM OF PYRIMIDINE COMPOUND, AND PREPARATION METHODS THEREFOR

(71) Applicant: Sichuan Kelun-Biotech Biopharmaceutical Co., Ltd., Chengdu (CN)

(72) Inventors: Zheng Gong, Chengdu (CN); Hongming Li, Chengdu (CN); Shidong Yi, Chengdu (CN); Long Li, Chengdu (CN); Tianming Wang, Chengdu (CN); Pingyun Chen, Chengdu (CN); Chengxi Yang, Chengdu (CN); Tao Wang, Chengdu (CN); Yaoyao Song, Chengdu (CN); Jiangfeng Zhou, Chengdu (CN); Yufeng Liang, Chengdu (CN); Zhonghui Chen, Chengdu (CN); Qiang Tian, Chengdu (CN); Hongmei Song, Chengdu (CN); Tongtong Xue, Chengdu (CN); Jingyi Wang, Chengdu (CN)

(73) Assignees: Sichuan Kelun-Biotech Biopharmaceutical Co., Ltd., Sichuan (CN); Ellipses Pharma Ltd, London (GB)

( * ) Notice: Subject to any disclaimer, the term of this patent is extended or adjusted under 35 U.S.C. 154(b) by 585 days.

(21) Appl. No.: 18/017,104

(22) PCT Filed: Jul. 23, 2021

(86) PCT No.: PCT/CN2021/108032
§ 371 (c)(1),
(2) Date: Jan. 20, 2023

(87) PCT Pub. No.: WO2022/022398
PCT Pub. Date: Feb. 3, 2022

(65) Prior Publication Data

US 2023/0295174 A1 Sep. 21, 2023

(30) Foreign Application Priority Data

Jul. 28, 2020 (CN) ........................ 202010737039.7

(51) Int. Cl.
*C07D 487/08* (2006.01)

(52) U.S. Cl.
CPC ........ *C07D 487/08* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 7,691,855 B2 | 4/2010 | Furet et al. | |
| 7,803,801 B2 | 9/2010 | Kodama et al. | |
| 7,960,568 B2 | 6/2011 | Diaz-Fernandez | |
| 10,023,570 B2 | 7/2018 | Andrews et al. | |
| 10,287,285 B2 | 5/2019 | Huggins et al. | |
| 10,478,425 B2 | 11/2019 | Tamura et al. | |
| 11,168,090 B2 | 11/2021 | Andrews et al. | |
| 2006/0205731 A1 | 9/2006 | Kodama et al. | |
| 2008/0234267 A1* | 9/2008 | Lackey | A61P 35/00 514/235.2 |
| 2013/0035331 A1 | 2/2013 | Moussy et al. | |
| 2013/0225548 A1 | 8/2013 | Fujihara et al. | |
| 2013/0281431 A1 | 10/2013 | Charifson et al. | |
| 2013/0289020 A1 | 10/2013 | Savory et al. | |
| 2014/0113882 A1 | 4/2014 | Breslin et al. | |
| 2018/0022732 A1 | 1/2018 | Brubaker et al. | |
| 2019/0010122 A1 | 1/2019 | Gibson et al. | |
| 2022/0135582 A1 | 5/2022 | Hong et al. | |
| 2022/0144847 A1* | 5/2022 | Chen | C07D 401/04 |

FOREIGN PATENT DOCUMENTS

| | | |
|---|---|---|
| CN | 101166734 A | 4/2008 |
| CN | 103298788 A | 9/2013 |
| CN | 108349969 A | 7/2018 |
| CN | 110267960 A | 9/2019 |
| CN | 111285882 A | 6/2020 |
| CN | 111484479 A | 8/2020 |

(Continued)

OTHER PUBLICATIONS

CAS Registry No. 1349069-14-2, 2-Pyridinamine, N-[6-[2-(4-methoxy-1-piperazinyl)-5-thiazolyl]-2- pyridinyl]-4-methyl-, 1 page, (Entered STN: Dec. 5, 2011).

(Continued)

*Primary Examiner* — Kamal A Saeed
*Assistant Examiner* — Quincy McKoy
(74) *Attorney, Agent, or Firm* — Choate, Hall & Stewart LLP; Kristen C. Buteau

(57) ABSTRACT

Provided are a salt and a crystal form of a pyrimidine compound, and preparation methods therefor. Specifically, provided are a salt and a crystal form of a compound I, including a crystal form of the salt, and preparation methods therefor.

I

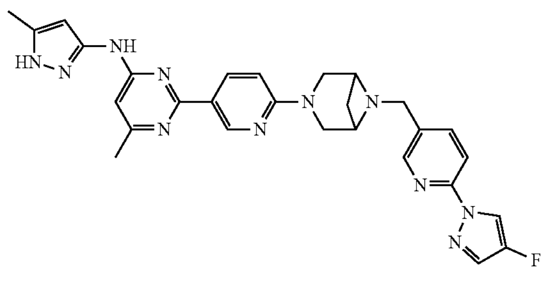

24 Claims, 15 Drawing Sheets

(56) References Cited

FOREIGN PATENT DOCUMENTS

| | | | | |
|---|---|---|---|---|
| CN | 111606886 A | 9/2020 | | |
| CN | 112279836 A | 1/2021 | | |
| CN | 112574201 A | 3/2021 | | |
| CN | 113135896 A | 7/2021 | | |
| EA | 201890318 A1 | 8/2018 | | |
| EP | 2634176 A1 | 9/2013 | | |
| EP | 4316490 A1 | 2/2024 | | |
| JP | 2013-517244 A | 5/2013 | | |
| RU | 2363699 C2 | 8/2009 | | |
| WO | WO-2006/067614 A2 | 6/2006 | | |
| WO | WO-2006/093247 A1 | 9/2006 | | |
| WO | WO-2008/146914 A1 | 12/2008 | | |
| WO | WO-2011/115183 A1 | 9/2011 | | |
| WO | WO-2012/057262 A1 | 5/2012 | | |
| WO | WO-2012/154518 A1 | 11/2012 | | |
| WO | WO-2016/127074 A1 | 8/2016 | | |
| WO | WO-2017/011776 A1 | 1/2017 | | |
| WO | WO-2017/079140 A1 | 5/2017 | | |
| WO | WO-2017/161269 A1 | 9/2017 | | |
| WO | WO-2018/011169 A1 | 1/2018 | | |
| WO | WO-2018/017983 A1 | 1/2018 | | |
| WO | WO-2018/022761 A1 | 2/2018 | | |
| WO | WO-2019/075108 A1 | 4/2019 | | |
| WO | WO-2019/143977 A1 | 7/2019 | | |
| WO | WO-2019/243303 A1 | 12/2019 | | |
| WO | WO-2020/035065 A1 | 2/2020 | | |
| WO | WO-2020/083311 A1 | 4/2020 | | |
| WO | WO-2020/083332 A1 | 4/2020 | | |
| WO | WO-2020/114388 A1 | 6/2020 | | |
| WO | WO-2020/114474 A1 | 6/2020 | | |
| WO | WO-2020/156319 A1 | 8/2020 | | |
| WO | WO-2020/171606 A1 | 8/2020 | | |
| WO | WO-2020168939 A1 | * | 8/2020 | ................ A61P 1/00 |
| WO | WO-2020/175968 A1 | 9/2020 | | |
| WO | WO-2020/200314 A1 | 10/2020 | | |
| WO | WO-2020/207419 A1 | 10/2020 | | |
| WO | WO-2020/233641 A1 | 11/2020 | | |
| WO | WO-2020/235945 A1 | 11/2020 | | |
| WO | WO-2020/239568 A1 | 12/2020 | | |
| WO | WO-2020/242946 A1 | 12/2020 | | |
| WO | WO-2021/023209 A1 | 2/2021 | | |
| WO | WO-2022/199503 A1 | 9/2022 | | |

OTHER PUBLICATIONS

CAS Registry No. 1349252-44-3, 1-Piperidinecarboxamide, 4-[5-[6-[(4-methyl-2-pyridinyl) amino]-2- pyridinyl]-2-thiazolyl]-N-[2-(4-morpholinyl)ethyl]-, 1 page, (Entered STN: Dec. 5, 2011).

CAS Registry No. 1374201-58-7, 1-Piperazineacetic acid, 4-[6-[(4-cyano-2-pyridinyl)amino]-4-cyclopropyl[2,3'-bipyridin]-6'-yl]-, 1 page, (Entered STN: May 22, 2012).

CAS Registry No. 909343-99-3, 4-Piperidinecarboxamide, N-(2-methoxyethyl)-N-methyl-1-[5-[6-[(4-methyl-2- pyridinyl)amino]-2-pyridinyl]-2-thiazolyl]-, 1 page, (Entered STN: Oct. 2, 2006).

CAS Registry No. 909344-03-2, 4-Piperidineacetic acid, 1-[5-[6-[(4,6-dimethyl-2- pyridinyl) amino]-2- pyridinyl]-2-thiazolyl]-, 1 page, (Entered STN: Oct. 2, 2006).

CAS Registry No. 909344-04-3, 4-Piperidineacetic acid, 1-[5-[6-[(6-methyl-2-pyridinyl)amino]- 2- pyridinyl]-2-thiazolyl]-, 1page, (Entered STN: Oct. 2, 2006).

CAS Registry No. 909344-08-7, 4-Piperidinecarboxylic acid, 1-[5-[6-(2-pyridinylamino)-2- pyridinyl]-2- thiazolyl]-, 1 page, (Entered STN: Oct. 2, 2006).

Li, B-K. et al., In silico prediction of spleen tyrosine kinase inhibitors using machine learning approaches and an optimized molecular descriptor subset generated by recursive feature elimination method, Computer in Biology and Medicine, 43:395-404, (2013).

Mulligan, Lois M., RET revisited: expanding the oncogenic portfolio, Nature Review, Cancer, 14:173-186, (2014).

Watanabe, M. et al., Dihydropyrrolo[2,3-d]pyrimidines: Selective Toll-Like Receptor 9 Antagonists from Scaffold Morphing Efforts, ACS Med. Chem. Lett., 5(11):1235-1239 (2014).

Lin, J.J. and Gainor, J.F., An early look at selective RET inhibitor resistance: new challenges and opportunities, Br. J. Cancer, 124(11):1757-1758 (2021).

Lin, J.J et al., Mechanisms of resistance to selective RET tyrosine kinase inhibitors in RET fusion-positive non-small-cell lung cancer, Ann. Oncol., 31(12):1725-1733 (2020).

Solomon, B.J et al., RET Solvent Front Mutations Mediate Acquired Resistance to Selective RET Inhibition in RET-Driven Malignancies, J. Thorac. Oncol., 15(4):541-549 (2020).

Subbiah, V. and Cote, G.J., Advances in Targeting RET-Dependent Cancers, Cancer Discov., 10(4):498-505 (2020).

Subbiah, V et al., Structural basis of acquired resistance to selpercatinib and pralsetinib mediated by non-gatekeeper RET mutations, Ann. Oncol., 32(2):261-268 (2021).

Tan, L. and Solomon, B.J., Defining resistance mechanisms to selective RET tyrosine kinase inhibitors in RET fusion-positive non-small-cell lung cancer, Ann. Oncol., 31(12):1599- 1600 (2020).

Jimenez, A.B. et al., Virtual Screening, In Silico Design and Evaluation of Dual ABC Protein and EGFR Ligands for the Treatment of Multidrug-Resistant Cancer, Proceedings of the 19th Lasallian Research, Development and Innovation Competition CLIDi 2017, 10 pages, English translation included, (2017).

Silverman, R.B., The Organic Chemistry of Drug Design and Drug Action, Table 2.2—Classical Isosteres, 5 pages, (2004).

Belikov, V.G., Pharmaceutical Chemistry, Moscow: MEDpress-inform, 8 pages, (2007).

Dobychin, Physical and Colloid Chemistry, English translation included, 29 pages, (1986).

Dyson, G. and May, P., Chemistry of Synthetic Drugs, MIR Publishing House, Moscow, 18 pages, (1964).

Kummerer, K., Pharmaceuticals in the Environment, Department of Environmental Health Sciences, University Medical Center, Freiburg, Germany, 19 pages, (2010).

Mashkovsky, M.D. and Sredstva, L., Medicaments: A Guide for Physicians, Moscow: Meditsina, Pt. 1, p. 8, 3 pages, (1993).

* cited by examiner

SALT AND CRYSTAL FORM OF PYRIMIDINE COMPOUND, AND PREPARATION METHODS THEREFOR

CROSS-REFERENCE TO RELATED APPLICATIONS

The present application is a 371 National Stage entry of International Application No. PCT/CN2021/108032, filed on Jul. 23, 2021, which claims priority to Chinese Patent (CN) application No. 202010737039.7, filed on Jul. 28, 2020, the entire contents of which is hereby incorporated by reference in its entirety.

TECHNICAL FIELD

The present invention relates to a salt and a crystal form of a pyrimidine compound, and a method for preparing the same. Specifically, the present invention relates to a salt and a crystal form of 2-(6-(6-((6-(4-fluoro-1H-pyrazol-1-yl) pyridin-3-yl)methyl)-3,6-diazabicyclo[3.1.1]heptan-3-yl) pyridin-3-yl)-6-methyl-N-(5-methyl-1H-pyrazol-3-yl)pyrimidin-4-amine (compound I) and a method for preparing the same, where the salt may also be various crystal forms.

BACKGROUND

Protein kinases are a class of enzymes catalyzing protein phosphorylation reactions. By mediating the process of cell signal transduction, protein phosphorylation regulates the physiological activities of cells, such as cell survival, proliferation, differentiation, apoptosis, and metabolism. The dysfunction of the protein kinases is closely associated with many diseases, including tumors, autoimmune diseases, inflammatory reactions, central nervous system diseases, cardiovascular diseases, diabetes, and the like.

As a protooncogene, RET encodes a RET protein that is a transmembrane receptor tyrosine protein kinase, and that consists of a cysteine-rich cadherin-like extracellular domain (for binding to ligands), a transmembrane domain, and an intracellular domain with tyrosine kinase activity. The activated RET protein can activate multiple downstream signal pathways, including RAS/RAF/ERK pathway, PI3K/Akt pathway, and JNK pathway, thereby resulting in cell proliferation, migration, and differentiation. The alteration (mutation or fusion) of the RET gene and the abnormal expression of wild-type RET gene lead to abnormal activation of RET proteins, such that the signal pathways are overactive, which is one of the main mechanisms of carcinogenesis. Abnormally activated RET proteins are involved in the proliferation and invasion of different tumor cells through a plurality of signal pathways, thereby affecting the tumor genesis and development. The alteration of the RET gene has a more significant effect on downstream cascade reactions, where the mutation of the RET gene is mainly associated with medullary thyroid cancer and papillary thyroid cancer, and the fusion of the RET gene is mainly associated with non-small cell lung cancer and chronic myeloid leukemia. Therefore, inhibiting the RET activity has great medical value (Nature Reviews Cancer, 2014, 14 (3): 173-86).

RET inhibitors have great potentials to treat and prevent a variety of diseases (such as tumor and irritable bowel syndrome). At present, five compounds are in a clinical trial stage, and compounds from many companies are in a preclinical research stage. However, at present, no inhibitors on the market are mainly targeted for RET. Therefore, it is necessary to develop a novel RET inhibitor with high efficacy and low toxicity to meet clinical needs.

In addition, since crystalline forms may have properties, such as bioavailability, physical and/or chemical stability, purity and/or manufacturability, that are more suitable for medical and pharmaceutical use under some conditions, it is expected to develop various crystalline forms of the RET inhibitors in the art.

SUMMARY

A first aspect of the present invention provides a salt of a compound I, including a fumarate salt of the compound I and a p-toluenesulfonate salt of the compound I,

I

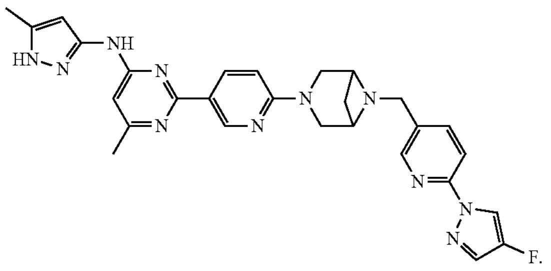

The salt of the compound I in the first aspect of the present invention may be various crystal forms, including crystal forms of the fumarate salt of the compound I and a crystal form of the p-toluenesulfonate salt of the compound I, such as a crystal form A of the fumarate salt of the compound I, a crystal form B of the fumarate salt of the compound I, a crystal form C of the fumarate salt of the compound I, a crystal form D of the fumarate salt of the compound I, a crystal form F of the fumarate salt of the compound I, a crystal form G of the fumarate salt of the compound 1, and a crystal form A of the p-toluenesulfonate salt of the compound 1.

A second aspect of the present invention provides a compound I, which is a crystalline form or an amorphous form, and is preferably a crystal form I, a crystal form II, a crystal form III, a crystal form IV, a crystal form V, or a crystal form VI.

A third aspect of the present invention provides a method for preparing a salt of a compound I, including reacting the compound I in any solid form with an inorganic acid or an organic acid, precipitating a solid, and subsequently separating and drying the precipitated solid.

A fourth aspect of the present invention provides a pharmaceutical composition, comprising the salt of the above compound I (for example, the fumarate salt or the p-toluenesulfonate salt of the compound I, especially the crystal form A, the crystal form B, the crystal form C, the crystal form D, the crystal form F, or the crystal form G of the fumarate salt of the compound I, or the crystal form A of the p-toluenesulfonate salt of the compound I) or the compound I in the above crystalline forms (for example, the crystal form I, the crystal form II, the crystal form III, the crystal form IV, the crystal form V, or the crystal form VI), and one or more pharmaceutically acceptable carriers.

A fifth aspect of the present invention provides a method for preventing or treating a disease or condition associated with RET activity, comprising administering to an individual in need thereof a therapeutically effective amount of the salt of the above compound I (for example, the fumarate salt or the p-toluenesulfonate salt of the compound I, especially the crystal form A, the crystal form B, the crystal form C, the crystal form D, the crystal form F, or the crystal form G of the fumarate salt of the compound I, or the crystal form A of the p-toluenesulfonate salt of the compound I) or the compound I in the above crystalline forms (for example, the crystal form I, the crystal form II, the crystal form III, the crystal form IV, the crystal form V, or the crystal form VI), or any combination thereof. Said disease or condition associated with RET activity is irritable bowel syndrome, or is cancer or tumor, including lung cancer (e.g., non-small cell lung cancer), breast cancer, head and neck cancer, rectal cancer, liver cancer, lymphoma, thyroid cancer (e.g., medullary thyroid cancer or papillary thyroid cancer), colon cancer, multiple myeloma, melanoma, glioma, brain tumor, or sarcoma.

A sixth aspect of the present invention provides use of the salt of the above compound I (for example, the fumarate salt or the p-toluenesulfonate salt of the compound I, especially the crystal form A, the crystal form B, the crystal form C, the crystal form D, the crystal form F, or the crystal form G of the fumarate salt of the compound I or the crystal form A of the p-toluenesulfonate salt of the compound I) or the compound I in the above crystalline forms (for example, the crystal form I, the crystal form II, the crystal form III, the crystal form IV, the crystal form V, or the crystal form VI), or any combination thereof, or a pharmaceutical composition comprising the same in the preparation of a drug for preventing or treating a disease or condition associated with RET activity. Said disease or condition associated with RET activity is irritable bowel syndrome, or is cancer or tumor, including lung cancer (e.g., non-small cell lung cancer), breast cancer, head and neck cancer, rectal cancer, liver cancer, lymphoma, thyroid cancer (e.g., medullary thyroid cancer or papillary thyroid cancer), colon cancer, multiple myeloma, melanoma, glioma, brain tumor, or sarcoma.

A seventh aspect of the present invention provides use of the salt of the above compound I (for example, the fumarate salt or the p-toluenesulfonate salt of the compound I, especially the crystal form A, the crystal form B, the crystal form C, the crystal form D, the crystal form F, or the crystal form G of the fumarate salt of the compound I, or the crystal form A of the p-toluenesulfonate salt of the compound I) or the compound I in the above crystalline form (for example, the crystal form I, the crystal form II, the crystal form III, the crystal form IV, the crystal form V, or the crystal form VI), or any combination thereof, or the pharmaceutical composition comprising the same for preventing or treating a disease or condition associated with RET activity. Said disease or condition associated with RET activity is irritable bowel syndrome, or is cancer or tumor, including lung cancer (e.g., non-small cell lung cancer), breast cancer, head and neck cancer, rectal cancer, liver cancer, lymphoma, thyroid cancer (e.g., medullary thyroid cancer or papillary thyroid cancer), colon cancer, multiple myeloma, melanoma, glioma, brain tumor, or sarcoma.

The compound I of the present invention has a desirable inhibitory effect on RET, and has desirable properties, such as pharmacokinetic properties and safety. In addition, the use of some solvents and/or methods for producing crystalline forms of the compound I or a salt thereof have been found. These crystalline forms, including substantially pure forms and mixtures of substantially pure forms, show one or more advantageous features. For example, they may offer advantages in respect of bioavailability and stability, and are suitable for use as active ingredients in pharmaceutical preparations. In particular, the various crystalline forms of the compound I and the fumarate salt and the p-toluenesulfonate salt thereof provide, e.g., one or more of the following advantages: improving the manufacturing process of the compound I, increasing the bioavailability and/or stability of the compound I, improving the solubility of the compound I, improving the hygroscopicity of the compound, and/or improving the stability and extending the shelf life of a pharmaceutical preparation comprising the compound I.

DETAILED DESCRIPTION OF THE INVENTION

Figure 1:
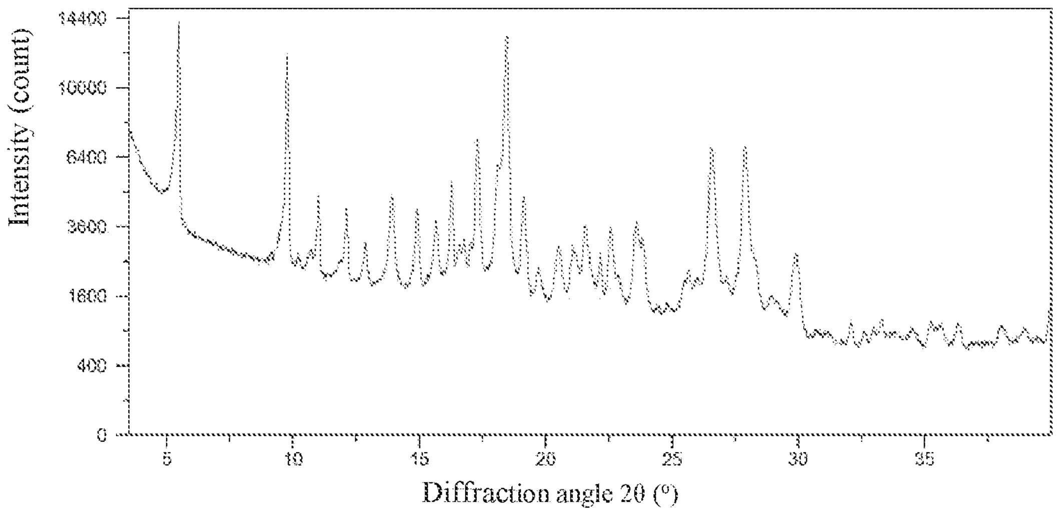
FIG. 1 shows an X-ray powder diffraction (XRPD) pattern of a crystal form A of a fumarate salt of a compound I prepared in Method 1 of Example 2.

The present invention is further explained below, and it should be understood that the terms are intended for descriptive purposes, instead of imposing any limitation on the present invention.

Definitions

Unless otherwise indicated, all technical terms and scientific terms used herein have the same meaning as commonly understood by those skilled in the art the present invention belongs to. In case of any discrepancy, the definitions herein shall prevail. When an amount, concentration, or other value or parameter is expressed in terms of a range, preferred range, or preferred numerical value upper limit and preferred numerical value lower limit, it should be understood to be equivalent to specific disclosure of any range by combining any pair of upper range limit or preferred numerical value with any lower range limit or preferred numerical value. Unless otherwise indicated, the numerical range set forth herein is intended to include endpoints of the range and all integers and fractions (decimals) within that range.

The term "about," when used in combination with a numerical variable, generally means that the numerical value of that variable and all numerical values of that variable are within an experimental error (e.g., within 95% confidence interval for the mean) or within ±20%, ±10%, ±5%, or ±2% range of a specified numerical value.

The term "comprising" or similar synonymous expressions, such as "including," "containing," and "having," are open-ended and do not exclude additional unrecited elements, steps or ingredients. The expression "composed of" excludes any unspecified element, step, or ingredient.

The term "substantially composed of" means that the range is limited to specified elements, steps or ingredients, with the addition of optionally existing elements, steps or ingredients that will not essentially affect the basic and novel features of the claimed subject matter. It should be understood that the term "comprising" and similar terms encompass the terms "substantially composed of" and "composed of."

The term "optional" or "optionally" used herein means that the subsequently described event or circumstance may or may not occur, and that the description includes instances where the event or circumstance occurs, and instances where the event or circumstance does not occur.

Unless otherwise indicated, all percentages, parts, etc. herein are by weight.

As used herein, the term "crystal form" or "crystal" refers to any solid substance that presents three-dimensional ordering, and as opposed to an amorphous solid substance, produces a characteristic XRPD pattern with well-defined peaks.

As used herein, the term "seed crystal" refers to an additive that can form a crystal nucleus to accelerate or promote the growth of crystal of an enantiomer of the same crystal form or stereoconfiguration as the additive in a crystallization process.

As used herein, the term "X-ray powder diffraction pattern" or "XRPD pattern" refers to an experimentally observed diffraction pattern or a parameter, data, or a value derived therefrom. The XRPD pattern is usually characterized by peak positions (abscissas) and/or peak intensities (ordinates).

As used herein, the term "diffraction angle" or "20" refers to a peak position expressed in degrees (°) based on X-ray diffraction experiment setting, and is usually an abscissa unit in a diffraction pattern. If the reflection is diffracted when the incident beam forms a 0 angle with some lattice plane, it is necessary to record the reflected beam at a 20 angle in the experimental setting. It should be understood that the reference herein to a specific 20 value for a specific crystal form is intended to denote a 20 value (expressed in degrees) measured using the X-ray diffraction experiment conditions described herein. For example, Cu-Kα (Kα1 (Å): 1.5406) monochromatic radiation is used as described herein. The XRPD patterns herein are preferably collected on an X-ray powder diffraction analyzer (PANalytacal X'Pert3 Powder), and preferably collected on the X-ray powder diffraction analyzer (PANalytacal X'Pert3 Powder) in a transmission mode.

As used herein, the term "substantially the same" or "substantially as shown in FIG. X" for X-ray diffraction peaks is intended to take into account representative peak positions and intensity variations. For example, those skilled in the art will understand that the peak position (20) will show some variations, usually as much as from 0.1 to 0.2 degree, and the instrument used for measuring diffraction will also cause some variations. In addition, those skilled in the art will understand that relative peak intensities will vary due to inter-instrument variability as well as the crystallinity degree, preferred orientation, prepared sample surface, and other factors known to those skilled in the art.

Similarly, as used herein, the reference herein to "substantially as shown in FIG. X" for a DSC pattern and a TGA pattern is also intended to encompass variations associated with these analysis techniques known to those skilled in the art. For example, there will usually be variations up to ±0.2° C. for well-defined peaks in a DSC pattern, and even greater variations (e.g., up to ±1° C.) for broad peaks.

As used herein, the term "room temperature" refers to 20° C.±5° C.

As used herein, the term "prevention" includes inhibiting and delaying the onset of a disease, and includes not only prevention before a disease develops, but also preventing the recurrence of a disease after treatment.

As used herein, the term "treating" refers to reversing, alleviating, or eliminating a targeted disease or disorder. If a subject receives a therapeutic amount of a salt of a compound of the present invention, or a compound thereof in a crystalline form, or a pharmaceutical composition of the present invention, and then at least one indicator and symptom of the subject exhibits observable and/or detectable alleviation and/or amelioration, the subject has been successfully "treated." It is understandable that the treatment includes not only complete treatment, but also achievement of some biologically or medically relevant result in spite of failure to achieve complete treatment. Specifically, the "treating" means that a salt of a compound of the present invention, or a compound thereof in a crystalline form, or a pharmaceutical composition of the present invention can achieve at least one of the following effects: (1) inhibiting a disease in an animal that is experiencing or exhibiting pathology or symptomology of the disease (i.e., restraining further development of pathology or symptomology); and (2) ameliorating a disease in an animal that is experiencing or exhibiting pathology or symptomology of the disease (i.e., reversing pathology and/or symptomology).

Salts and Crystalline Forms Thereof

The present invention provides a salt of a compound I, where said salt is selected from a fumarate salt and a p-toluenesulfonate salt

I

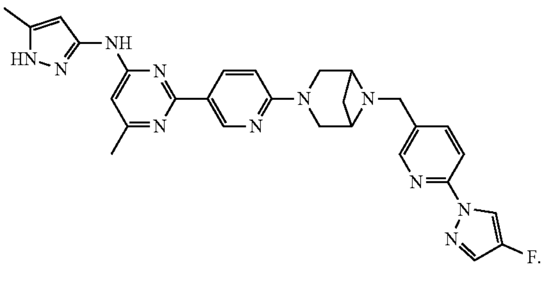

In some embodiments, a salt of the compound I is a fumarate salt of the compound I, where a molar ratio of the compound I to fumaric acid is 1:1.

Crystal Form A of Fumarate Salt of Compound I

In some embodiments, the salt of the compound I is the crystal form A of the fumarate salt of the compound I, an XRPD pattern of which exhibits at least two, at least three, at least four, at least five, or at least six diffraction angles 2θ (°) at maximum intensity.

In some embodiments, an XRPD pattern of the crystal form A of the fumarate salt of the compound I comprises diffraction peaks at 2θ of about 5.44±0.2°, 9.75±0.2°, and/or 18.43±0.2°. Preferably, the XRPD pattern of the crystal form A of the fumarate salt of the compound I further comprises diffraction peaks at 2θ of about 17.28±0.2°, 18.13±0.2°, 26.55±0.2°, and/or 27.86±0.2°. More preferably, the XRPD pattern of the crystal form A of the fumarate salt of the compound I further comprises diffraction peaks at 2θ of about 10.99±0.2°, 12.09 0.2°, 13.89±0.2°, 14.87±0.2°, 16.25±0.2°, and/or 19.11±0.2°. Still more preferably, the XRPD pattern of the crystal form A of the fumarate salt of the compound I further comprises diffraction peaks at 2θ of about 15.63±0.2°, 20.48±0.2°, 21.55±0.2°, 22.14±0.2°, 22.55±0.2°, 23.56±0.2°, 23.83±0.2°, and/or 29.86±0.2°. Yet more preferably, the XRPD pattern of the crystal form A of the fumarate salt of the compound I further comprises diffraction peaks at 2θ of about 12.84±0.2°, 16.56±0.2°, 16.74±0.2°, 17.02±0.2°, 19.70±0.2°, 21.08±0.2°, and/or 25.64±0.2°.

In some embodiments, the XRPD pattern of the crystal form A of the fumarate salt of the compound I is substantially as shown in FIG. 1, and is preferably as shown in FIG. 1.

Figure 2:
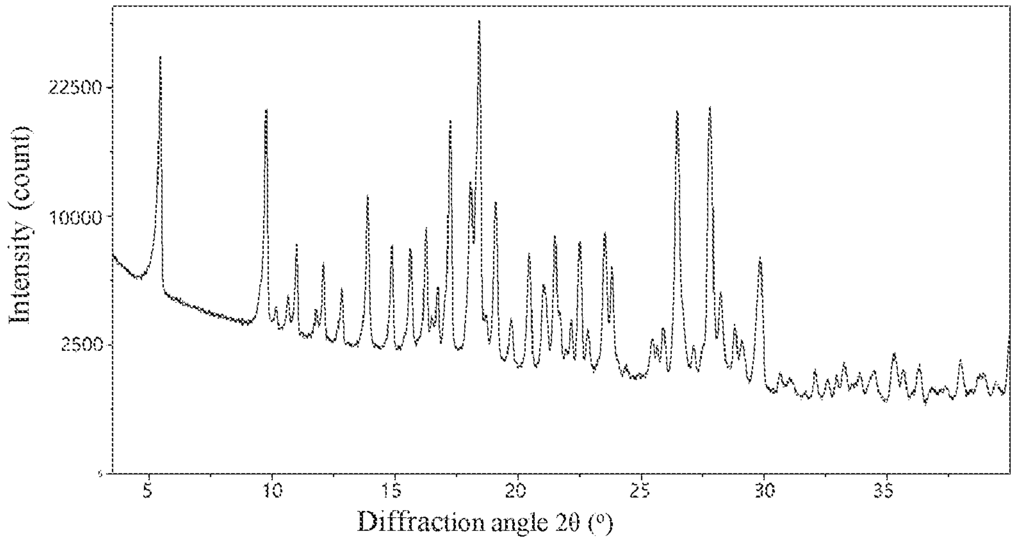
FIG. 2 shows an XRPD pattern of a crystal form A of a fumarate salt of the compound I prepared in Example 7.

In some embodiments, the XRPD pattern of the crystal form A of the fumarate salt of the compound 1 is substantially as shown in FIG. 2, and is preferably as shown in FIG. 2.

Figure 3A:
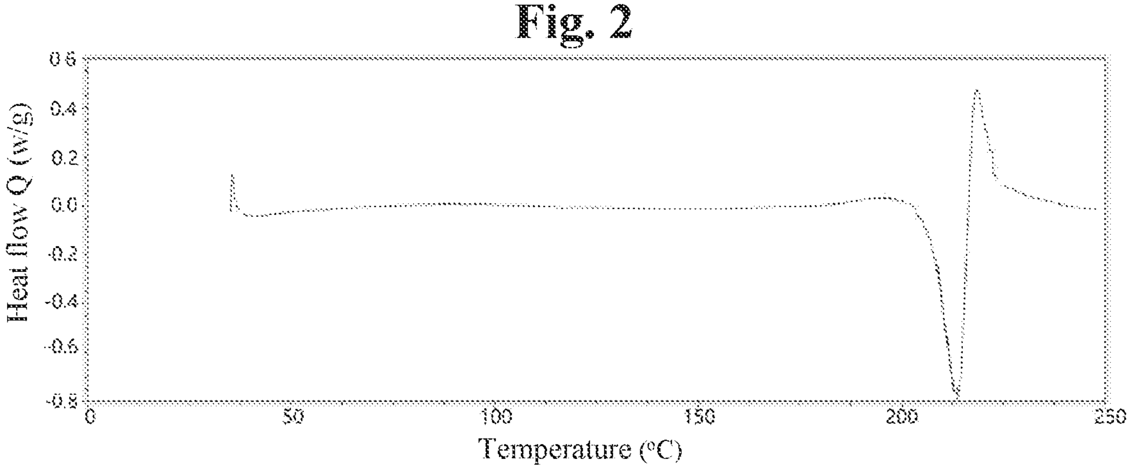
FIG. 3A shows a differential scanning calorimetry (DSC) pattern of the crystal form A of the fumarate salt of the compound I prepared in Example 7.

In some embodiments, an onset temperature of an endothermic peak of the crystal form A of the fumarate salt of the compound I is about 206.5° C.±5° C., and is preferably about 206.5° C.±2° C.; and preferably, a DSC pattern of the crystal form A of the fumarate salt of the compound I is substantially as shown in FIG. 3A, and is preferably as shown in FIG. 3A.

Figure 3B:
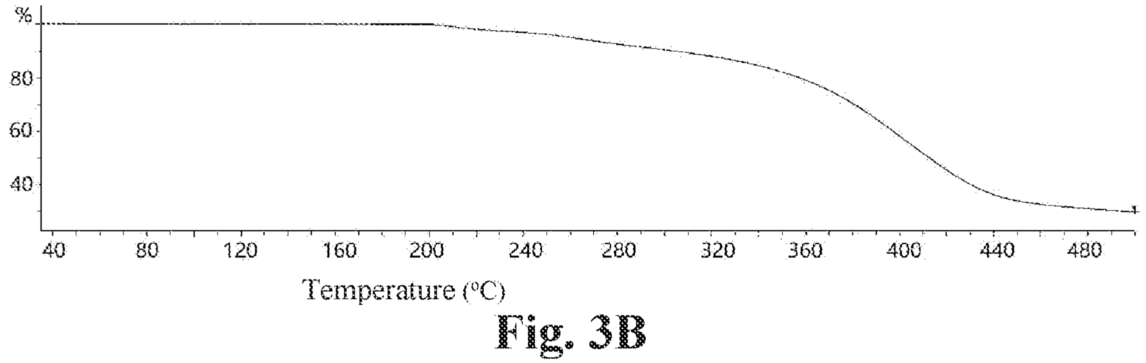
FIG. 3B shows a thermogravimetric analysis (TGA) pattern of the crystal form A of the fumarate salt of the compound I prepared in Example 7.

In some embodiments, a TGA pattern of the crystal form A of the fumarate salt of the compound 1 is substantially as shown in FIG. 3B, and is preferably as shown in FIG. 3B.

In some embodiments, the crystal form A of the fumarate salt of the compound I is an anhydrate.

In some embodiments, a molar ratio of the compound 1 to fumaric acid in the crystal form A of the fumarate salt of the compound I is 1:1.

In some embodiments, the crystal form A of the fumarate salt of the compound I has two or all of the following properties:

(a) the XRPD pattern substantially as shown in FIG. 2;

(b) the DSC pattern substantially as shown in FIG. 3A; and (c) the TGA pattern substantially as shown in FIG. 3B.

Crystal Form B of Fumarate Salt of Compound I

In some embodiments, a salt of the compound I is the crystal form B of the fumarate salt of the compound I, an XRPD pattern of which exhibits at least two, at least three, at least four, at least five, or at least six diffraction angles 2θ (°) at maximum intensity.

In some embodiments, the XRPD pattern of the crystal form B of the fumarate salt of the compound I comprises diffraction peaks at 2θ of about 9.12±0.2°, 16.57±0.2°, 24.78±0.2°, and/or 25.74±0.2°. Preferably, the XRPD pattern of the crystal form B of the fumarate salt of the compound I further comprises diffraction peaks at 2θ of about 15.64±0.2°, 18.05±0.2°, 21.13±0.2°, and/or 22.08±0.2°. More preferably, the XRPD pattern of the crystal form B of the fumarate salt of the compound I further comprises diffraction peaks at 2θ of about 13.62±0.2°, 15.29±0.2°, 21.81±0.2°, 25.58±0.2°, and/or 26.91±0.2°. Still more preferably, the XRPD pattern of the crystal form B of the fumarate salt of the compound I further comprises diffraction peaks at 2θ of about 5.70±0.2°, 11.50±0.2°, 16.26±0.2°, 17.31±0.2°, 19.64±0.2°, 23.87±0.2°, and/or 27.24±0.2°.

Figure 4:
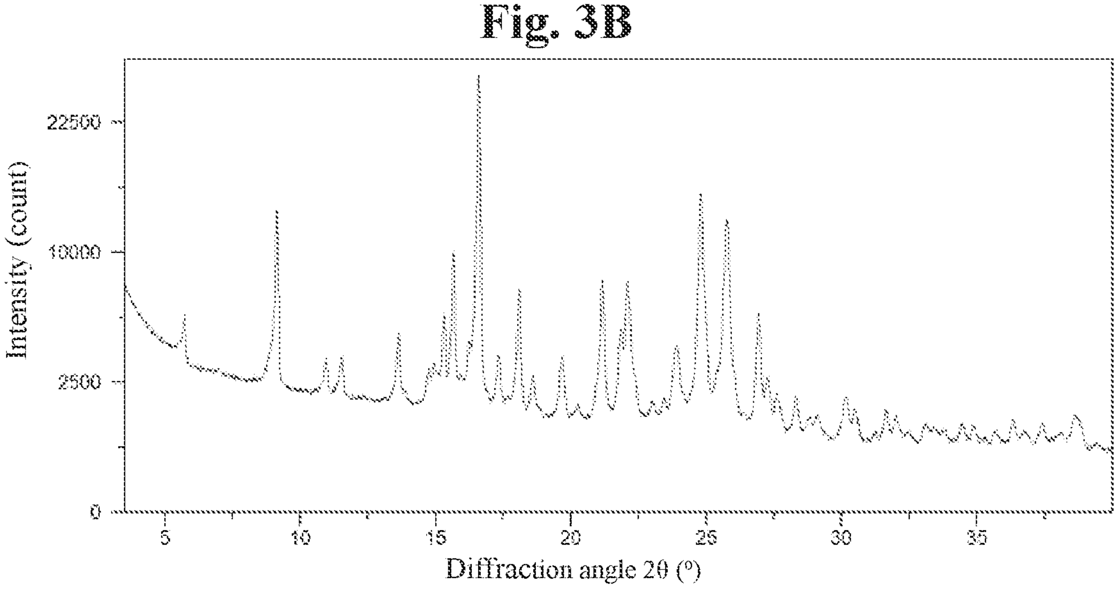
FIG. 4 shows an XRPD pattern of a crystal form B of a fumarate salt of the compound I prepared in Example 3.

In some embodiments, the XRPD pattern of the crystal form B of the fumarate salt of the compound I is substantially as shown in FIG. 4, and is preferably as shown in FIG. 4.

In some embodiments, an onset temperature of an endothermic peak of the crystal form B of the fumarate salt of the compound 1 is about 202.21° C.±5° C., and is preferably about 202.21° C.±2° C. More preferably, a DSC pattern of the crystal form B of the fumarate salt of the compound I is substantially as shown in FIG. 5, and is preferably as shown in FIG. 5.

Figure 5:
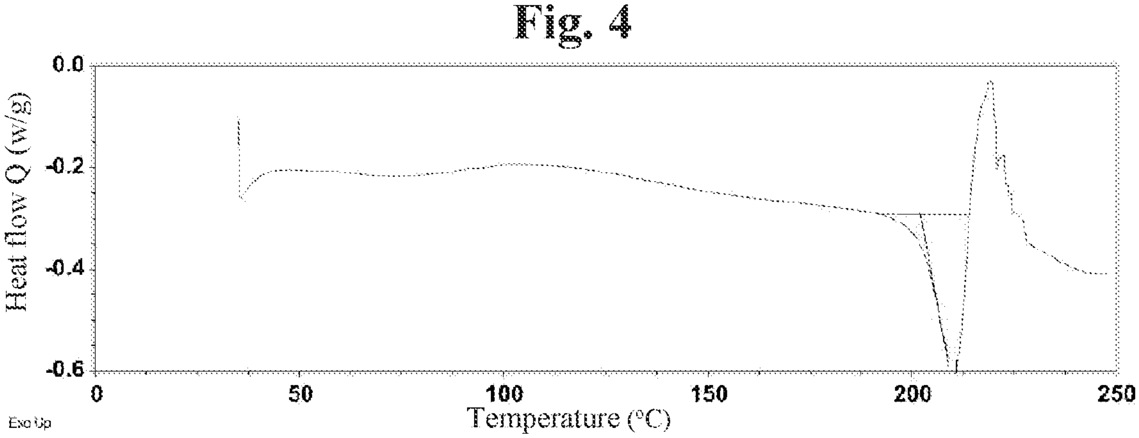
FIG. 5 shows a DSC pattern of the crystal form B of the fumarate salt of the compound I prepared in Example 3.

In some embodiments, the crystal form B of the fumarate salt of the compound I has the following two properties:

(a) the XRPD pattern substantially as shown in FIG. 4; and (b) the DSC pattern substantially as shown in FIG. 5.

Crystal Form C of Fumarate Salt of Compound I

In some embodiments, a salt of the compound I is the crystal form C of the fumarate salt of the compound I, an XRPD pattern of which exhibits at least two, at least three, at least four, at least five, or at least six diffraction angles 2θ (°) at maximum intensity.

In some embodiments, an XRPD pattern of the crystal form C of the fumarate salt of the compound I comprises diffraction peaks at 2θ of about 9.13±0.2° and/or 26.08±0.2°. Preferably, the XRPD pattern of the crystal form C of the fumarate salt of the compound I further comprises diffraction peaks at 2θ of about 11.09±0.2°, 17.63±0.2°, 18.08±0.2°, 20.21±0.2°, 22.31±0.2°, and/or 27.92:0.2°. More preferably, the XRPD pattern of the crystal form C of the fumarate salt of the compound I further comprises diffraction peaks at 2θ of about 10.05±0.2°, 13.27±0.2°, 13.78±0.2°, 14.39±0.2°, and/or 17.24±0.2°. Still more preferably, the XRPD pattern of the crystal form C of the fumarate salt of the compound I further comprises diffraction peaks at 2θ of about 8.58±0.2°, 16.84±0.2°, 23.12±0.2°, and/or 25.13±0.2°.

Figure 6:
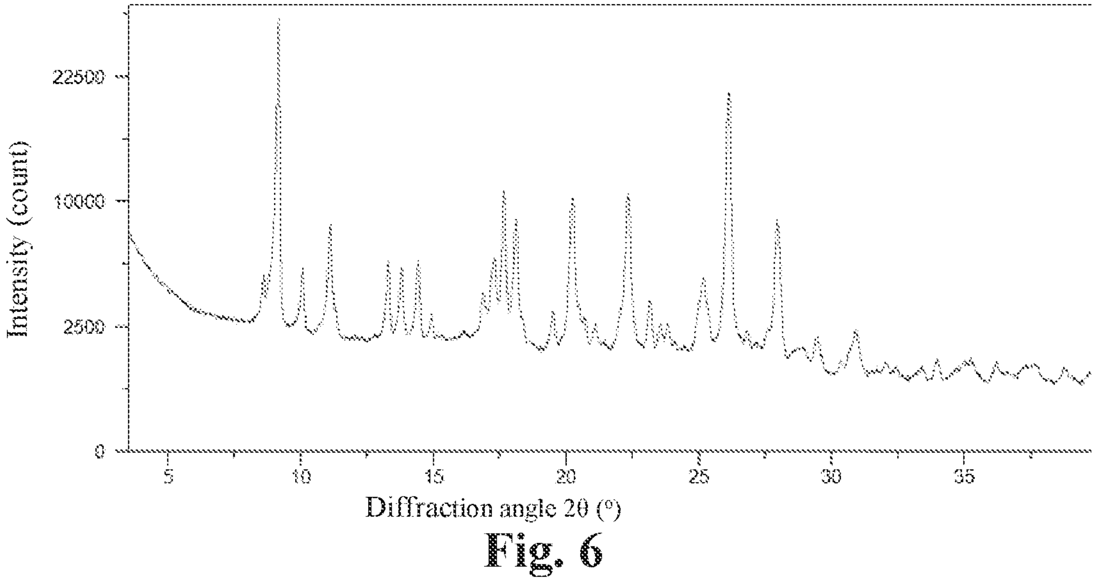
FIG. 6 shows an XRPD pattern of a crystal form C of a fumarate salt of the compound I prepared in Method 1 of Example 4.

In some embodiments, the XRPD pattern of the crystal form C of the fumarate salt of the compound I is substantially as shown in FIG. 6, and is preferably as shown in FIG. 6.

Figure 38:
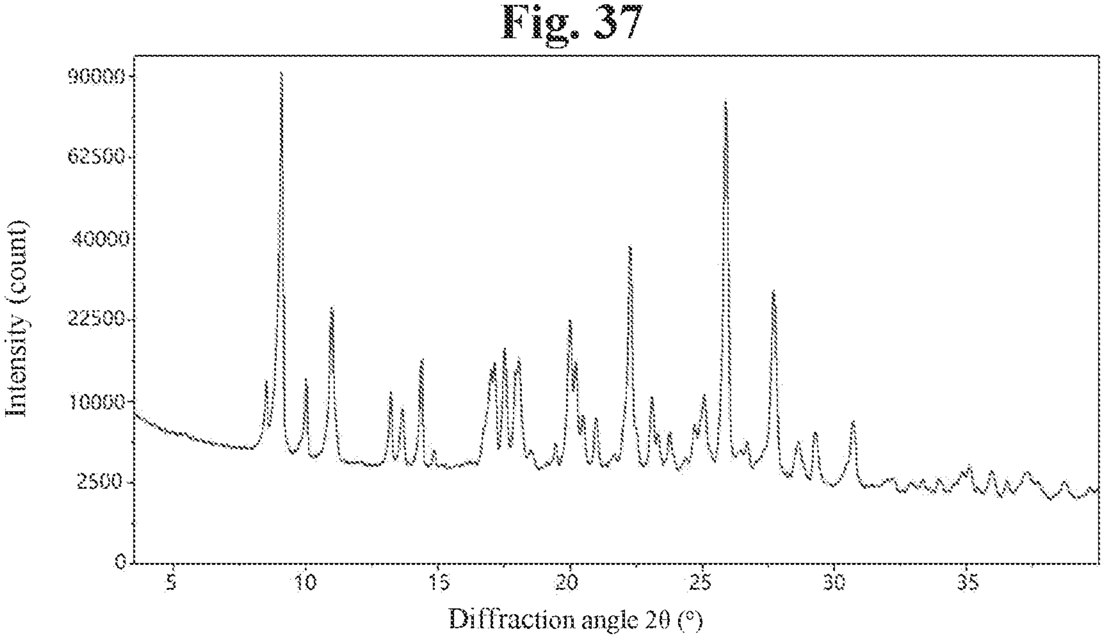
FIG. 38 shows an XRPD pattern of a crystal form C of a fumarate salt of the compound I prepared in Example 17.

In some embodiments, the XRPD pattern of the crystal form C of the fumarate salt of the compound I is substantially as shown in FIG. 38, and is preferably as shown in FIG. 38.

Figure 39:
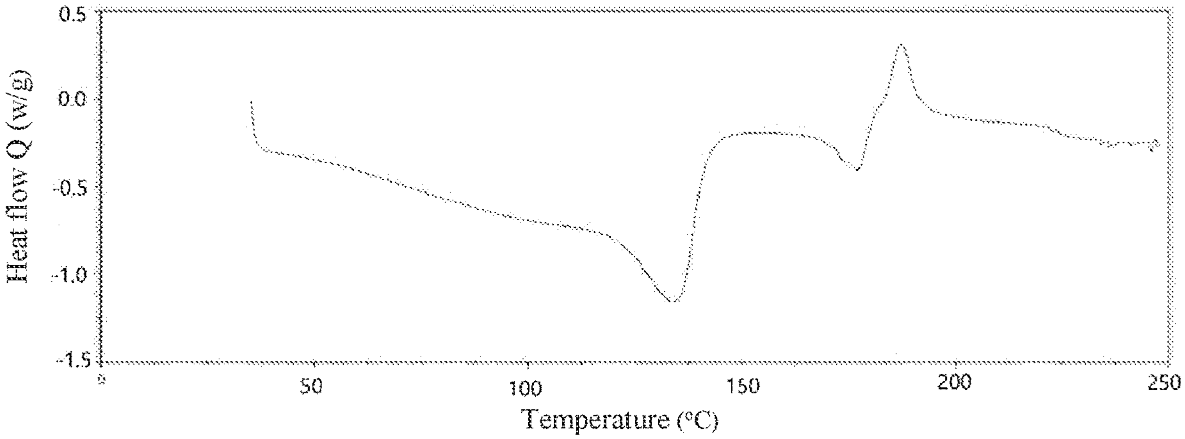
FIG. 39 shows a DSC pattern of the crystal form C of the fumarate salt of the compound I prepared in Example 17.

In some embodiments, a DSC pattern of the crystal form C of the fumarate salt of the compound I is substantially as shown in FIG. 39, and is preferably as shown in FIG. 39.

Figure 40:
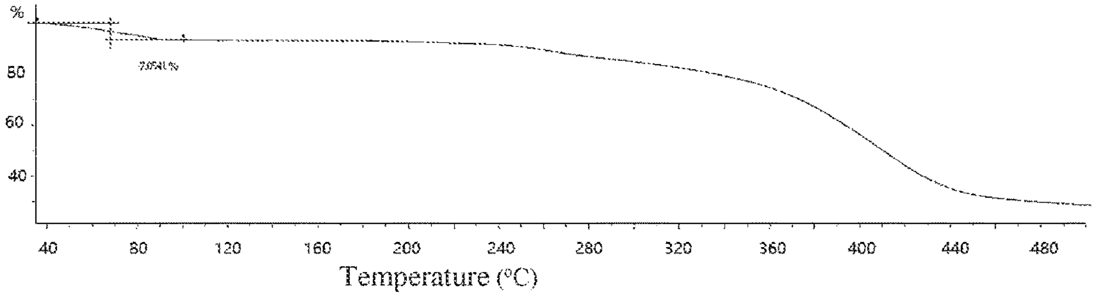
FIG. 40 shows a TGA pattern of the crystal form C of the fumarate salt of the compound I prepared in Example 17.

In some embodiments, a TGA pattern of the crystal form C of the fumarate salt of the compound I is substantially as shown in FIG. 40, and is preferably as shown in FIG. 40.

Crystal Form D of Fumarate Salt of Compound I

Figure 13:
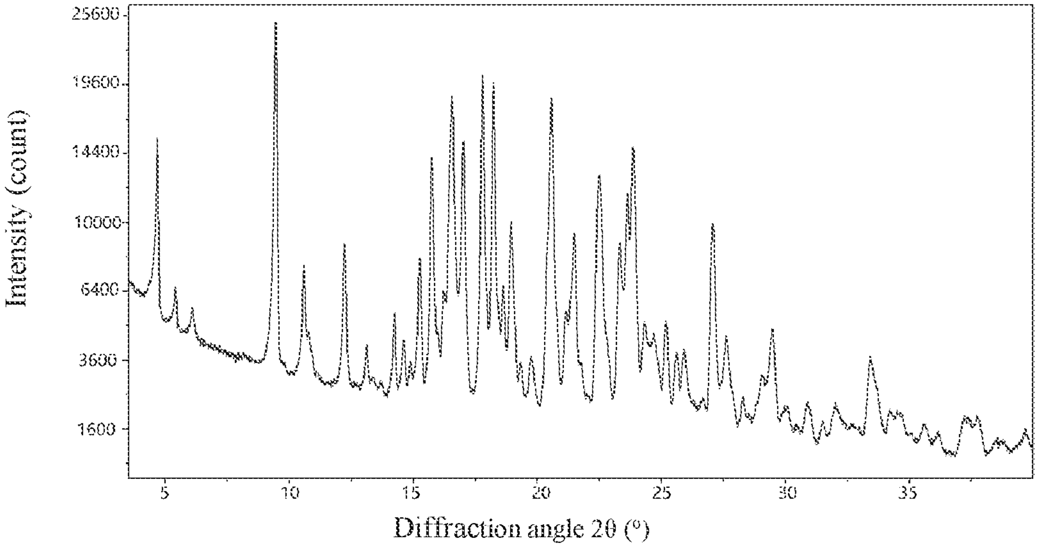
FIG. 13 shows an XRPD pattern of a crystal form D of a fumarate salt of the compound I prepared in Example 8.

In some embodiments, an XRPD pattern of the crystal form D of the fumarate salt of the compound I is substantially as shown in FIG. 13, and is preferably as shown in FIG. 13.

Figure 14:
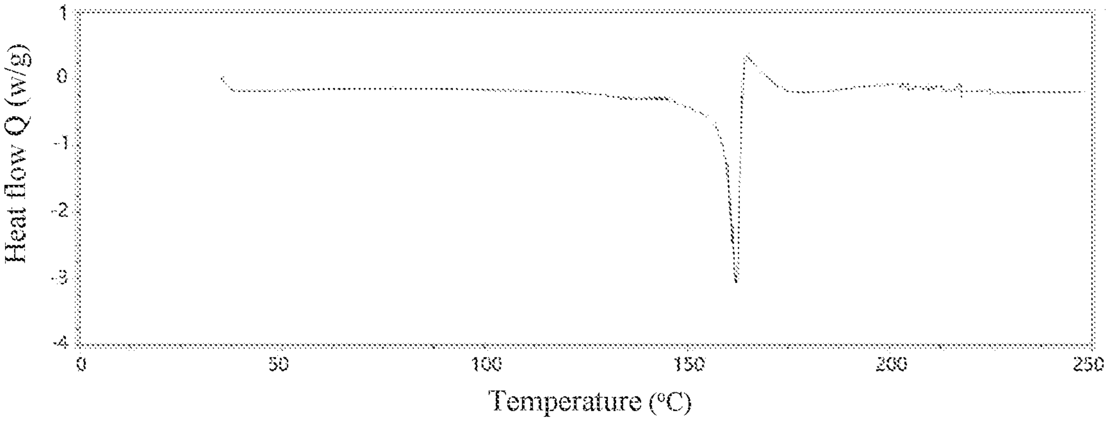
FIG. 14 shows a DSC pattern of the crystal form D of the fumarate salt of the compound I prepared in Example 8.

In some embodiments, a DSC pattern of the crystal form D of the fumarate salt of the compound I is substantially as shown in FIG. 14, and is preferably as shown in FIG. 14.

Figure 15:
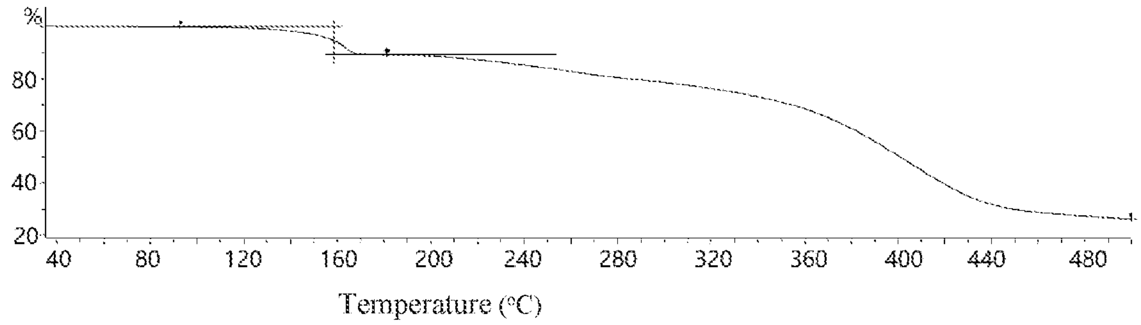
FIG. 15 shows a TGA pattern of the crystal form D of the fumarate salt of the compound I prepared in Example 8.

In some embodiments, a TGA pattern of the crystal form D of the fumarate salt of the compound I is substantially as shown in FIG. 15, and is preferably as shown in FIG. 15.

Crystal Form F of Fumarate Salt of Compound I

Figure 16:
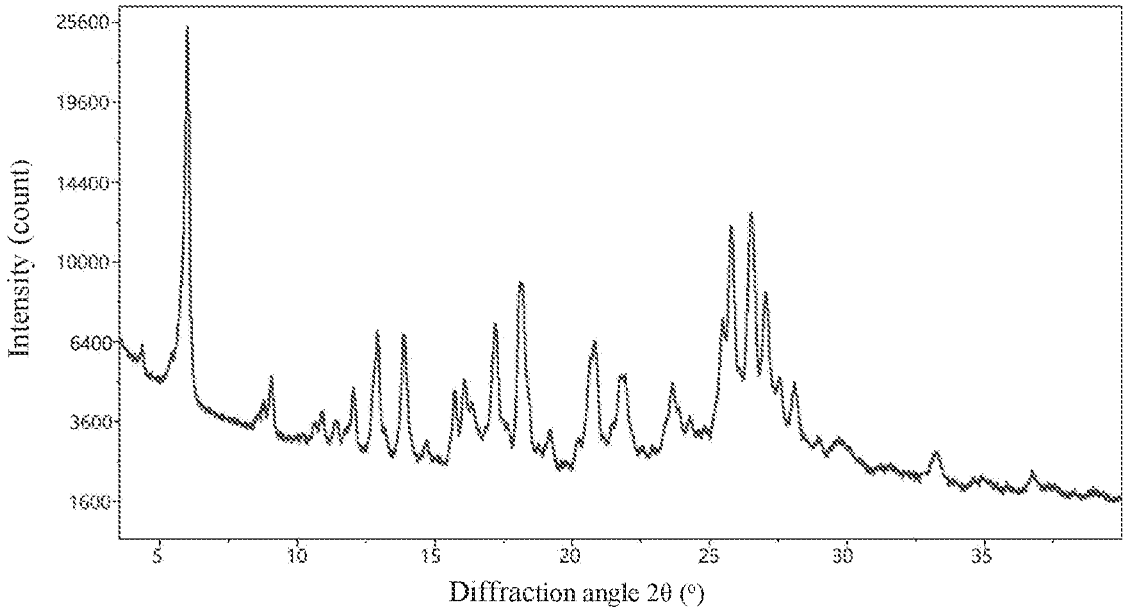
FIG. 16 shows an XRPD pattern of a crystal form F of a fumarate salt of the compound I prepared in Example 9.

In some embodiments, an XRPD pattern of the crystal form F of the fumarate salt of the compound I is substantially as shown in FIG. 16, and is preferably as shown in FIG. 16.

Figure 17:
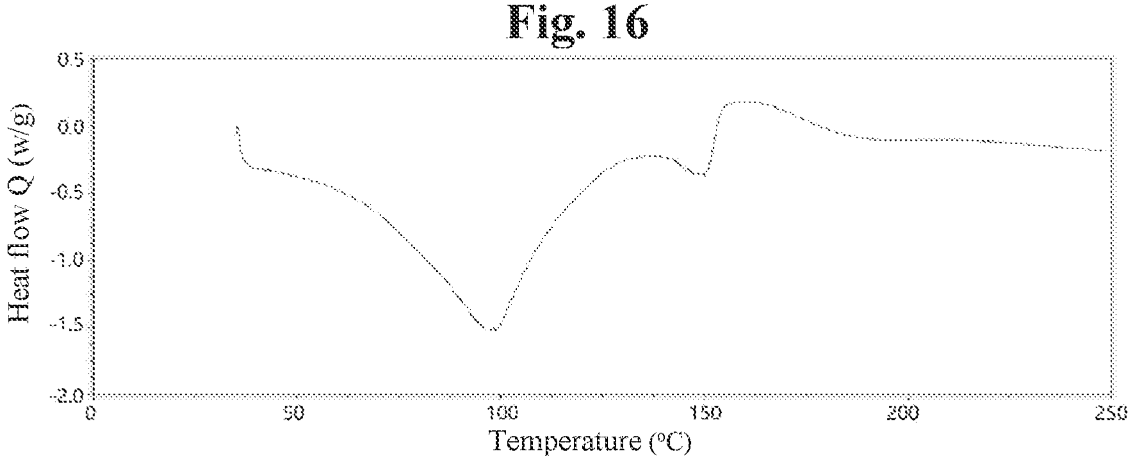
FIG. 17 shows a DSC pattern of the crystal form F of the fumarate salt of the compound I prepared in Example 9.

In some embodiments, a DSC pattern of the crystal form F of the fumarate salt of the compound I is substantially as shown in FIG. 17, and is preferably as shown in FIG. 17.

Figure 18:
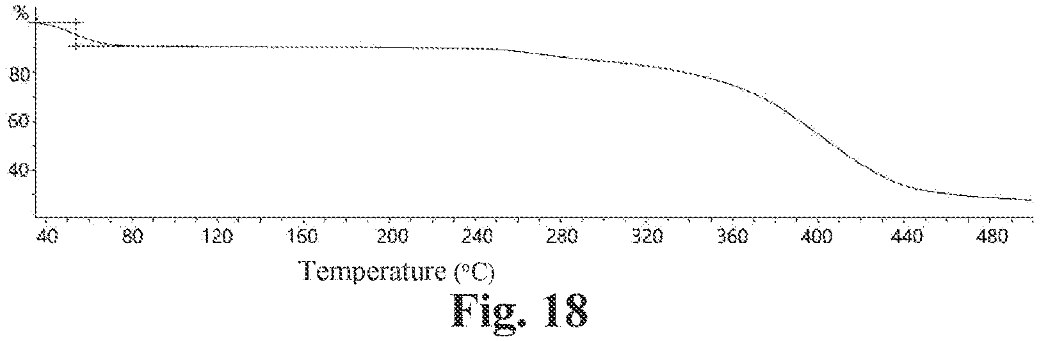
FIG. 18 shows a TGA pattern of the crystal form F of the fumarate salt of the compound I prepared in Example 9.

In some embodiments, a TGA pattern of the crystal form F of the fumarate salt of the compound I is substantially as shown in FIG. 18, and is preferably as shown in FIG. 18.

Crystal Form G of Fumarate Salt of Compound I

Figure 19:
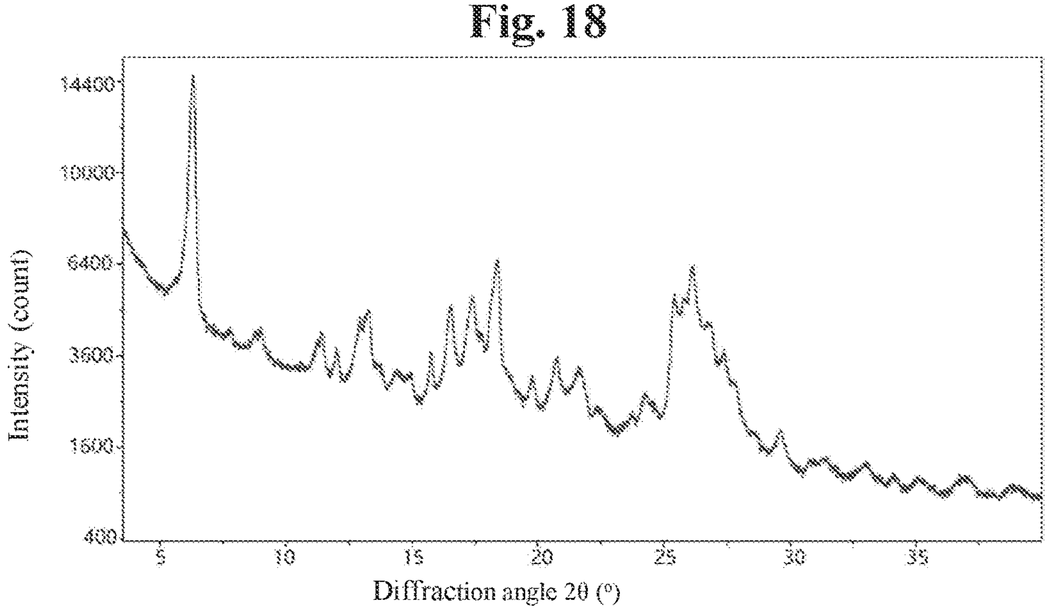
FIG. 19 shows an XRPD pattern of a crystal form G of a fumarate salt of the compound I prepared in Example 10.

In some embodiments, an XRPD pattern of the crystal form G of the fumarate salt of the compound I is substantially as shown in FIG. 19, and is preferably as shown in FIG. 19.

Figure 20:
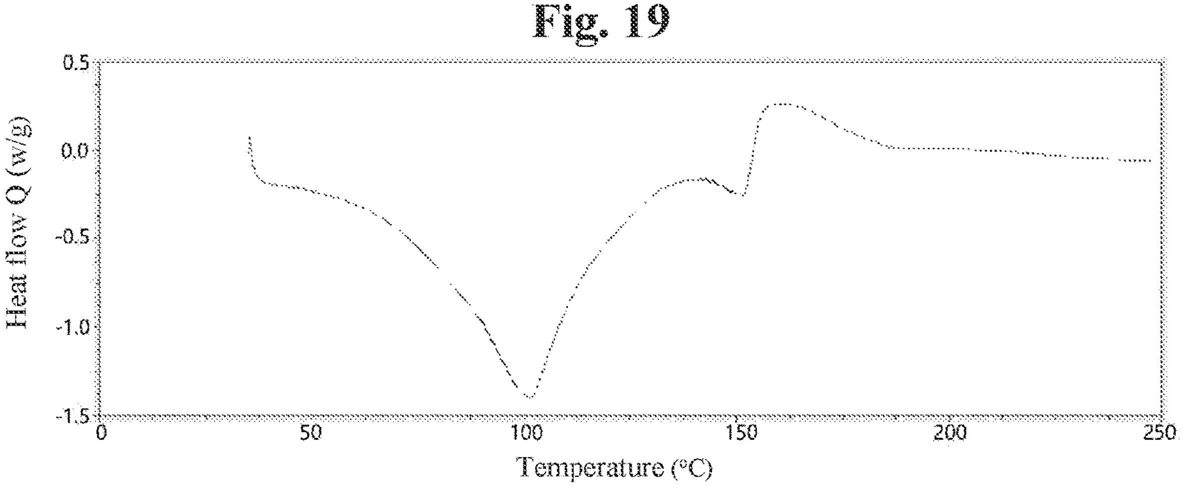
FIG. 20 shows a DSC pattern of the crystal form G of the fumarate salt of the compound I prepared in Example 10.

In some embodiments, a DSC pattern of the crystal form G of the fumarate salt of the compound I is substantially as shown in FIG. 20, and is preferably as shown in FIG. 20.

Figure 21:
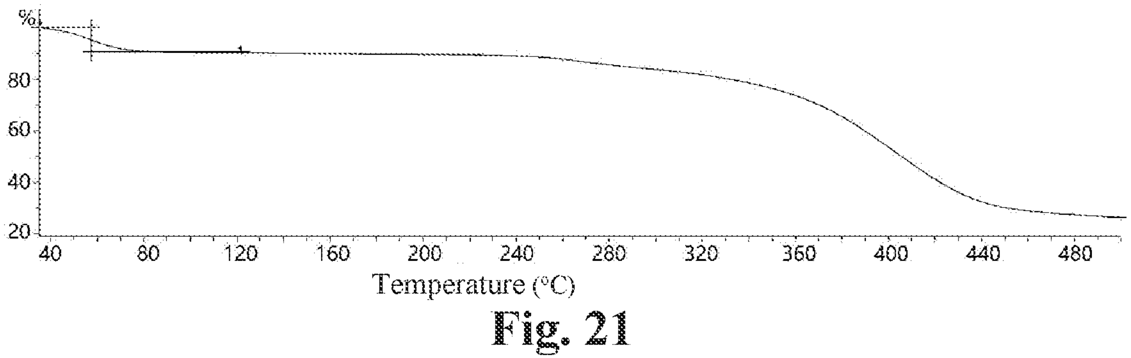
FIG. 21 shows a TGA pattern of the crystal form G of the fumarate salt of the compound I prepared in Example 10.

In some embodiments, a TGA pattern of the crystal form G of the fumarate salt of the compound I is substantially as shown in FIG. 21, and is preferably as shown in FIG. 21.

Crystal Form A of p-Toluenesulfonate Salt of Compound I

In some embodiments, a salt of the compound I is a crystal form A of the p-toluenesulfonate salt of the compound I, an XRPD pattern of which exhibits at least two, at least three, at least four, at least five, or at least six diffraction angles 2θ (°) at maximum intensity.

In some embodiments, the XRPD pattern of the crystal form A of the p-toluenesulfonate salt of the compound I comprises diffraction peaks at 2θ of about 4.69±0.2° and/or 13.87±0.2°. Preferably, the XRPD pattern of the crystal form A of the p-toluenesulfonate salt of the compound I further comprises diffraction peaks at 2θ of about 16.98±0.2°, 18.23±0.2°, 19.27±0.2°, 19.98±0.2°, 22.08±0.2°, 23.35±0.2°, and/or 25.78±0.2°. More preferably, the XRPD pattern of the crystal form A of the p-toluenesulfonate salt of the compound I further comprises diffraction peaks at 2θ of about 8.25±0.2°, 12.23±0.2°, 15.60±0.2°, 17.83±0.2°, 22.49±0.2°, 24.30±0.2°, 25.17±0.2°, and/or 28.13±0.2°. Still more preferably, the XRPD pattern of the crystal form A of the p-toluenesulfonate salt of the compound I further comprises diffraction peaks at 2θ of about 10.65±0.2°, 12.77±0.2°, and/or 20.84±0.2°.

Figure 7:
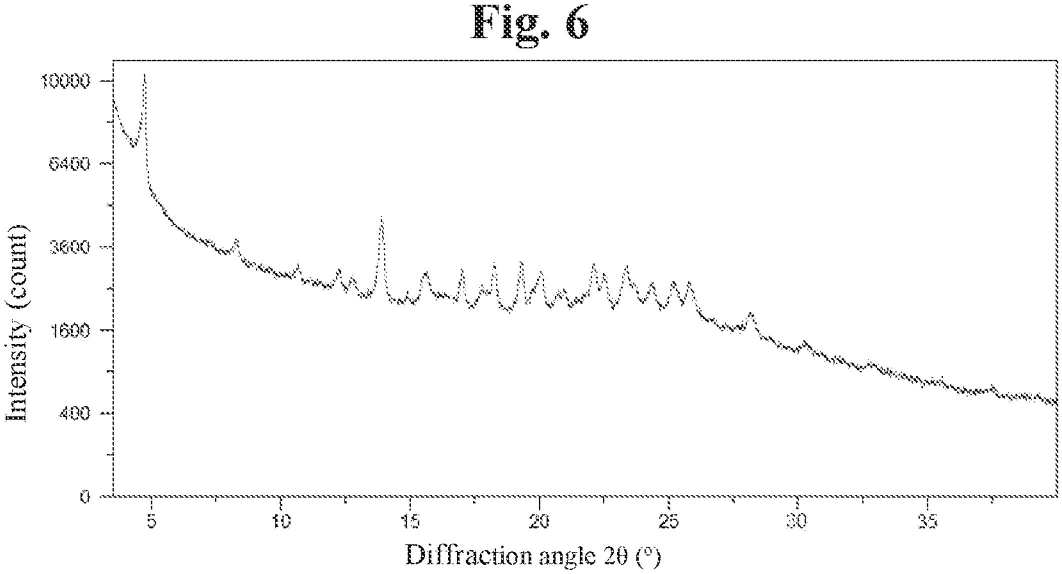
FIG. 7 shows an XRPD pattern of a crystal form A of a p-toluenesulfonate salt of the compound I prepared in Example 5.

In some embodiments, the XRPD pattern of the crystal form A of the p-toluenesulfonate salt of the compound I is substantially as shown in FIG. 7, and is preferably as shown in FIG. 7.

Figure 8:
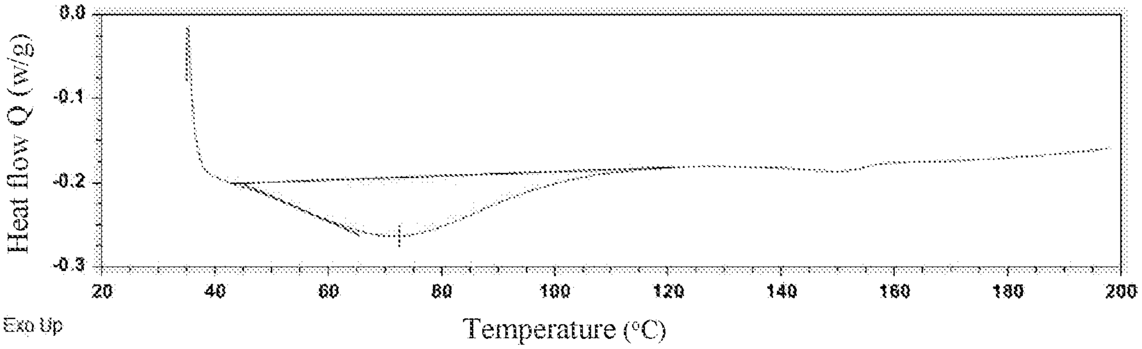
FIG. 8 shows a DSC pattern of the crystal form A of the p-toluenesulfonate salt of the compound I prepared in Example 5.

In some embodiments, an onset temperature of an endothermic peak of the crystal form A of the p-toluenesulfonate salt of the compound I is about 43.71° C.±5° C., and is preferably about 43.71° C.±2° C. More preferably, a DSC pattern of the crystal form A of the p-toluenesulfonate salt of the compound I is substantially as shown in FIG. 8, and is preferably as shown in FIG. 8.

Figure 9:
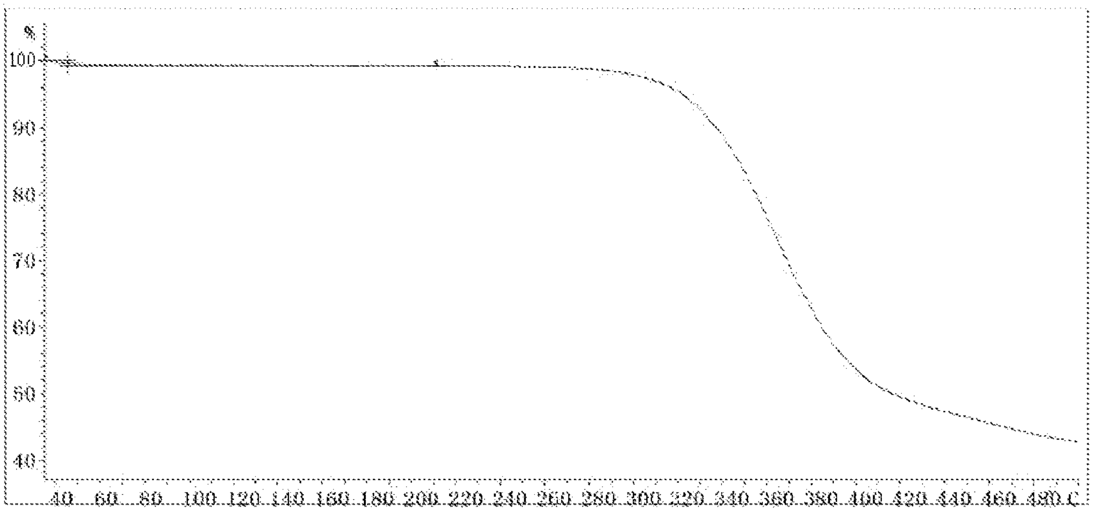
FIG. 9 shows a TGA pattern of the crystal form A of the p-toluenesulfonate salt of the compound I prepared in Example 5.

In some embodiments, the TGA pattern of the crystal form A of the p-toluenesulfonate salt of the compound I is substantially as shown in FIG. 9, and is preferably as shown in FIG. 9.

In some embodiments, the crystal form A of the p-toluenesulfonate salt of the compound I has two or all of the following properties:

(a) the XRPD pattern substantially as shown in FIG. 7;

(b) the DSC pattern substantially as shown in FIG. 8; and (c) the TGA pattern substantially as shown in FIG. 9.

Crystalline Form of Compound I

The present invention provides the compound I, which is a crystalline form.

Crystal Form I of Compound I

In some embodiments, the compound I is the crystal form I of the compound I, an XRPD pattern of which exhibits at least two, at least three, at least four, at least five, or at least six diffraction angles 2θ (°) at maximum intensity.

In some embodiments, the XRPD pattern of the crystal form I of the compound I comprises diffraction peaks at 2θ of about 18.00±0.2°, 19.55±0.2°, 22.62±0.2°, and/or 27.20±0.2°. Preferably, the XRPD pattern of the crystal form I of the compound I further comprises diffraction peaks at 2θ of about 5.53±0.2°, 15.95±0.2°, and/or 18.77±0.2°. More preferably, the XRPD pattern of the crystal form I of the compound I further comprises diffraction peaks at 2θ of about 14.12±0.2°, 14.89±0.2°, 16.89±0.2°, 20.13±0.2°, 20.36±0.2°, 21.71±0.2°, 24.86±0.2°, and/or 25.67±0.2°. Still more preferably, the XRPD pattern of the crystal form I of the compound I further comprises diffraction peaks at 2θ of about 11.18±0.2°, 12.33±0.2°, 12.67±0.2°, 12.95±0.2°, 14.46±0.2°, 18.36±0.2°, 20.87±0.2°, 25.13±0.2°, 26.16±0.2°, 26.84±0.2°, 27.80±0.2°, and/or 28.28±0.2°.

Figure 10:
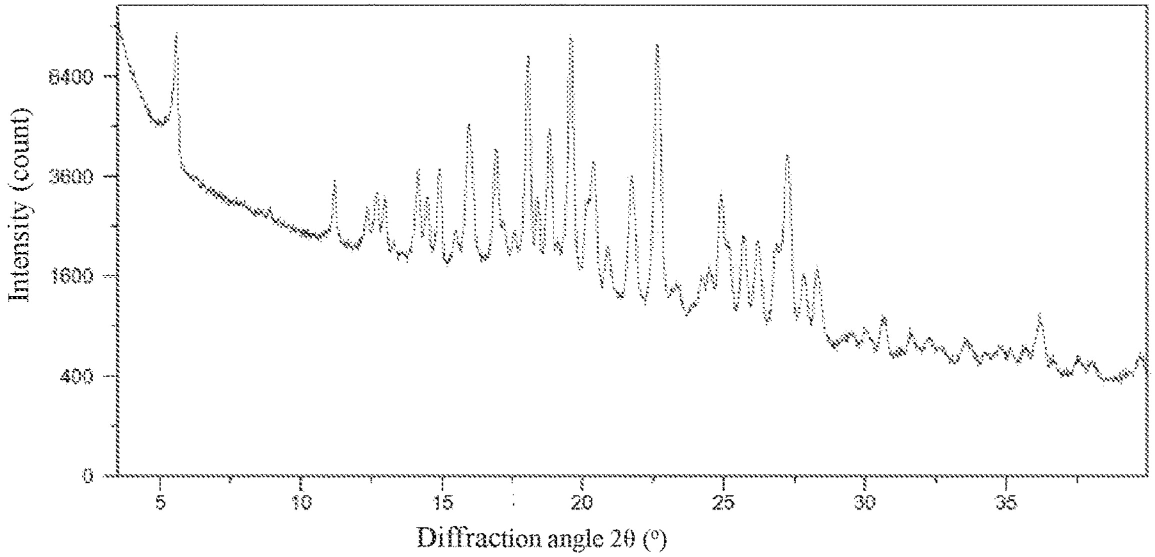
FIG. 10 shows an XRPD pattern of a crystal form I of the compound I prepared in Example 6.

In some embodiments, the XRPD pattern of the crystal form I of the compound I is substantially as shown in FIG. 10, and is preferably as shown in FIG. 10.

Figure 11:
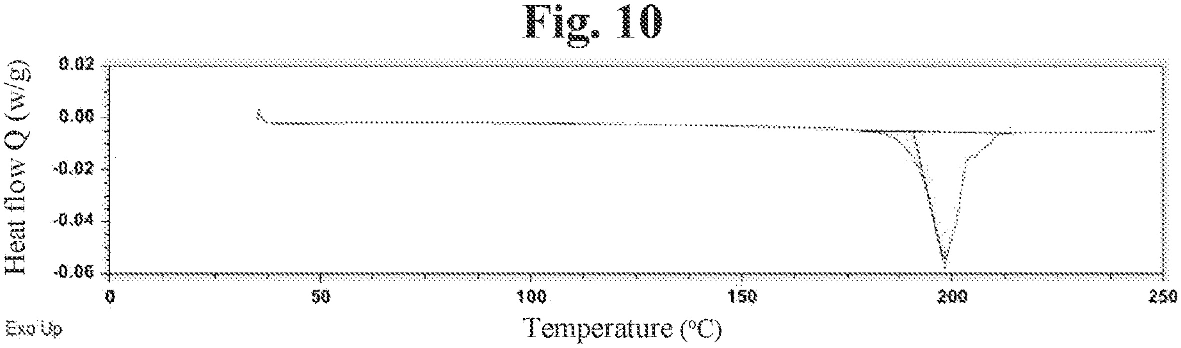
FIG. 11 shows a DSC pattern of the crystal form I of the compound I prepared in Example 6.

In some embodiments, an onset temperature of an endothermic peak of the crystal form I of the compound I is about 190.79° C.±5° C., and is preferably about 190.79° C.±2° C. More preferably, a DSC pattern of the crystal form I of the compound I is substantially as shown in FIG. 11, and is preferably as shown in FIG. 11.

Figure 12:
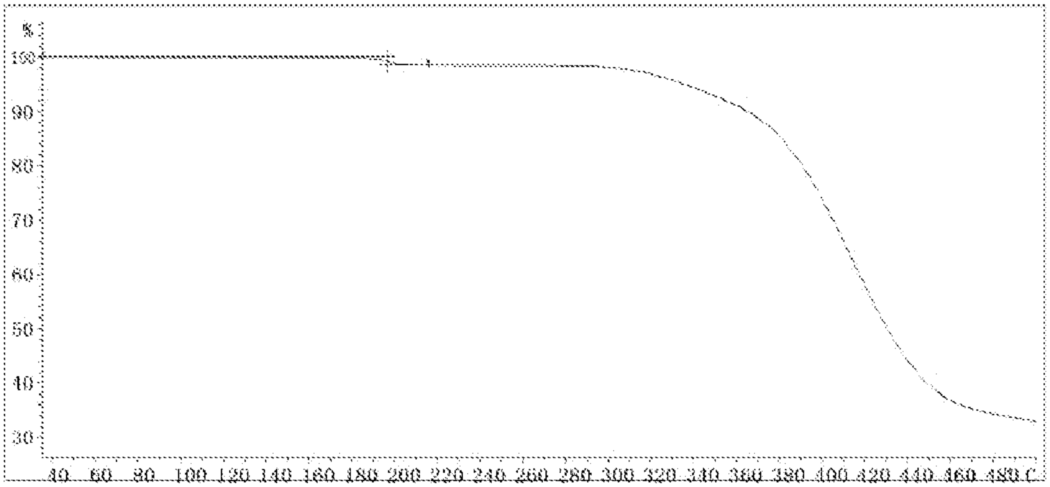
FIG. 12 shows a TGA pattern of the crystal form I of the compound I prepared in Example 6.

In some embodiments, a TGA pattern of the crystal form I of the compound I is substantially as shown in FIG. 12, and is preferably as shown in FIG. 12.

In some embodiments, the crystal form I of the compound I is an anhydrate.

In some embodiments, the crystal form I of the compound I has two or all of the following properties:

(a) the XRPD pattern substantially as shown in FIG. 10;

(b) the DSC pattern substantially as shown in FIG. 11; and (c) the TGA pattern substantially as shown in FIG. 12.

Crystal Form II of Compound I

In some embodiments, the compound I is a crystal form II of the compound I, an XRPD pattern of which exhibits at least two, at least three, or at least four diffraction angles 2θ (°) at maximum intensity.

In some embodiments, the XRPD pattern of the crystal form II of the compound I comprises diffraction peaks at 2θ of about 15.03±0.2°, 16.25±0.2°, 20.61±0.2°, 21.69±0.2°, and/or 22.61±0.2°.

Figure 22:
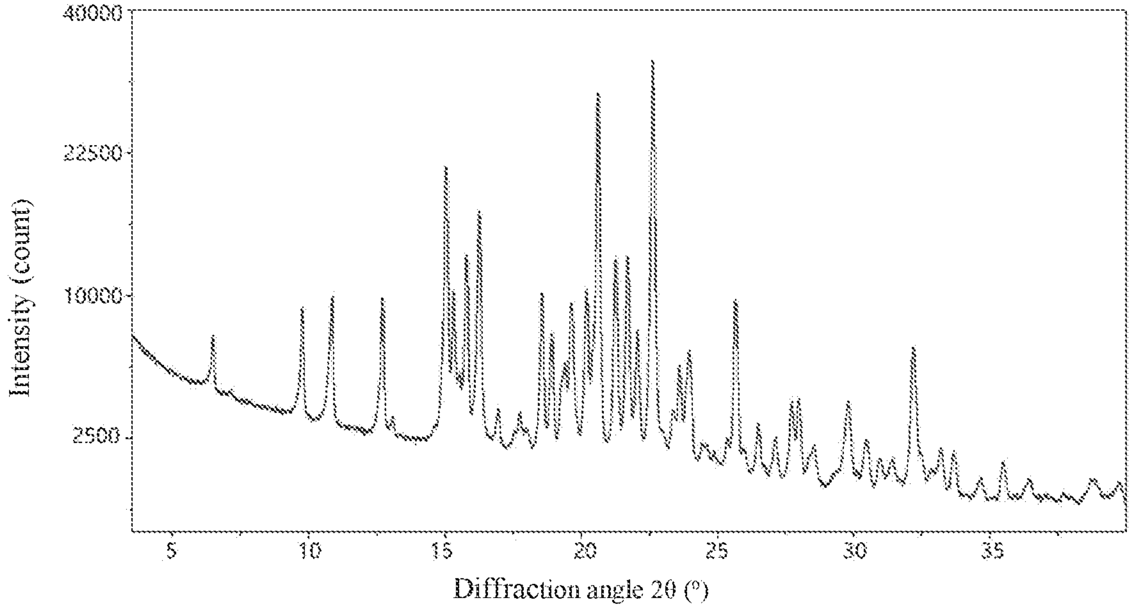
FIG. 22 shows an XRPD pattern of a crystal form II of the compound I prepared in Example 12.

In some embodiments, the XRPD pattern of the crystal form II of the compound I is substantially as shown in FIG. 22, and is preferably as shown in FIG. 22.

Figure 23:
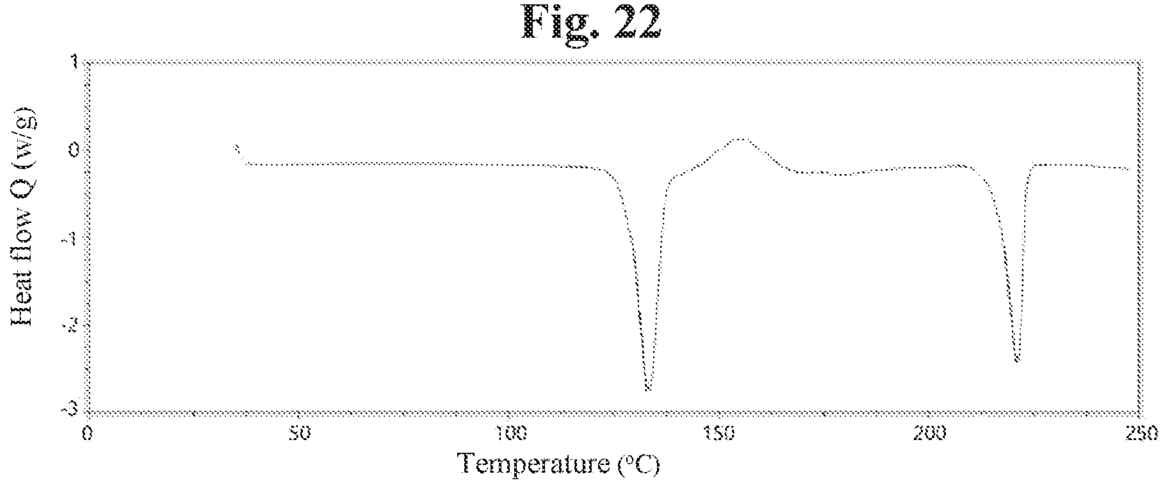
FIG. 23 shows a DSC pattern of the crystal form II of the compound I prepared in Example 12.

In some embodiments, an onset temperature of an endothermic peak of the crystal form II of the compound I is about 128.4° C.±5° C., and is preferably about 128.4° C.±2° C. More preferably, a DSC pattern of the crystal form I of the compound I is substantially as shown in FIG. 23, and is preferably as shown in FIG. 23.

Figure 24:
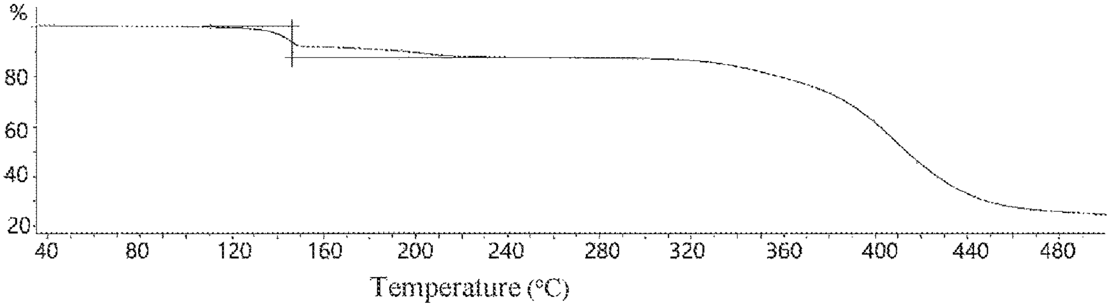
FIG. 24 shows a TGA pattern of the crystal form II of the compound I prepared in Example 12.

In some embodiments, a TGA pattern of the crystal form II of the compound I is substantially as shown in FIG. 24, and is preferably as shown in FIG. 24.

Crystal Form III of Compound I

Figure 25:
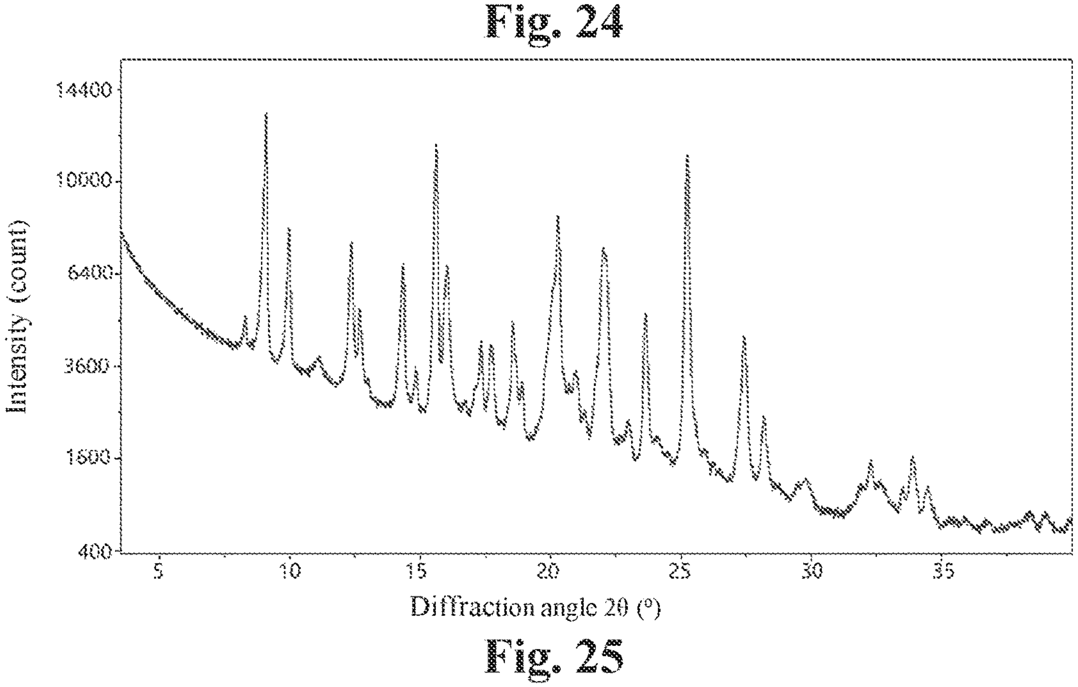
FIG. 25 shows an XRPD pattern of a crystal form III of the compound I prepared in Example 13.

In some embodiments, an XRPD pattern of the crystal form III of the compound I is substantially as shown in FIG. 25, and is preferably as shown in FIG. 25.

Figure 26:
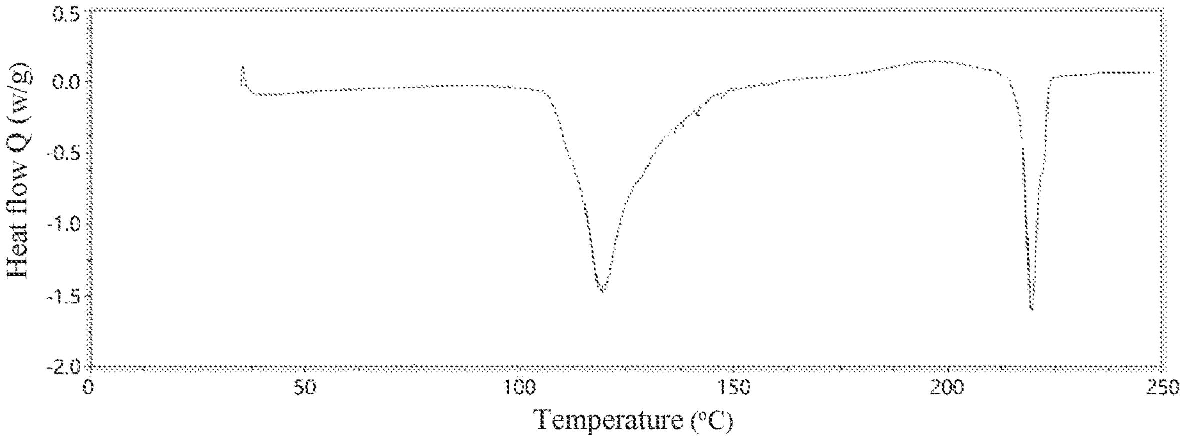
FIG. 26 shows a DSC pattern of the crystal form III of the compound I prepared in Example 13.

In some embodiments, a DSC pattern of the crystal form III of the compound I is substantially as shown in FIG. 26, and is preferably as shown in FIG. 26.

Figure 27:
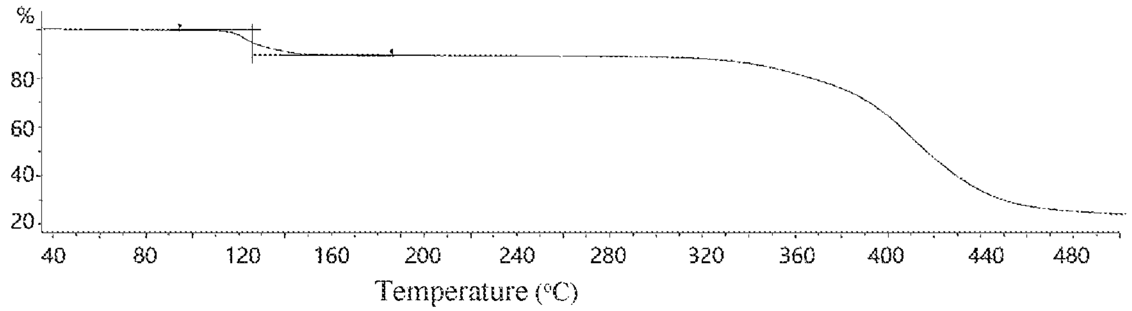
FIG. 27 shows a TGA pattern of the crystal form III of the compound I prepared in Example 13.

In some embodiments, a TGA pattern of the crystal form III of the compound I is substantially as shown in FIG. 27, and is preferably as shown in FIG. 27.

Crystal Form IV of Compound I

Figure 28:
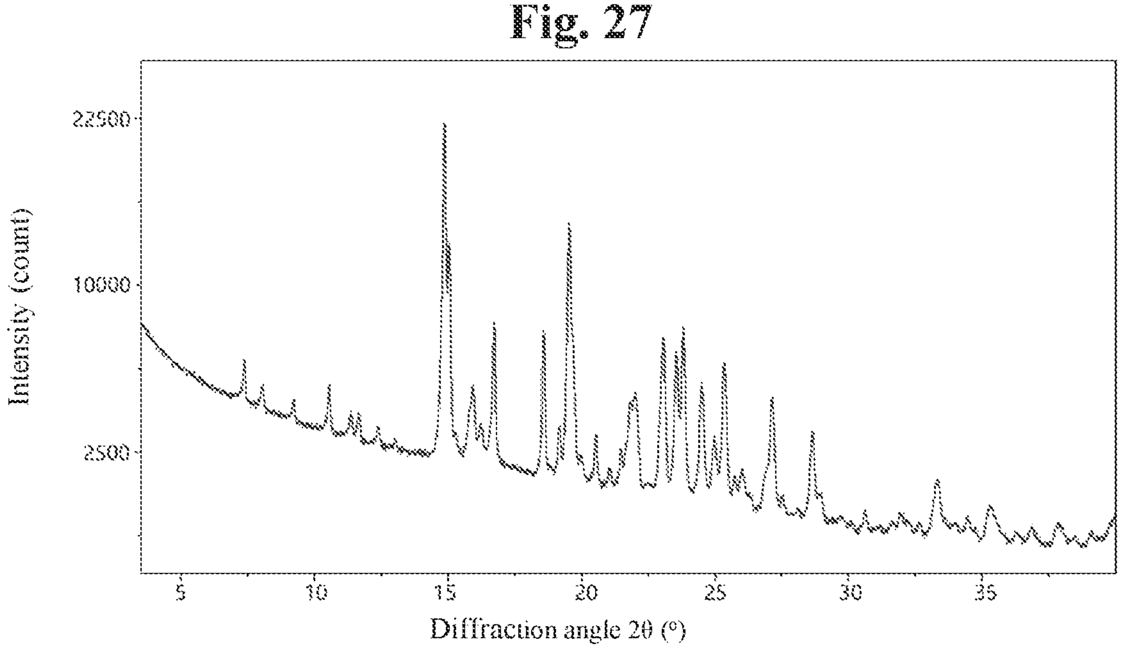
FIG. 28 shows an XRPD pattern of a crystal form IV of the compound I prepared in Example 14.

In some embodiments, an XRPD pattern of the crystal form IV of the compound I is substantially as shown in FIG. 28, and is preferably as shown in FIG. 28.

Figure 29:
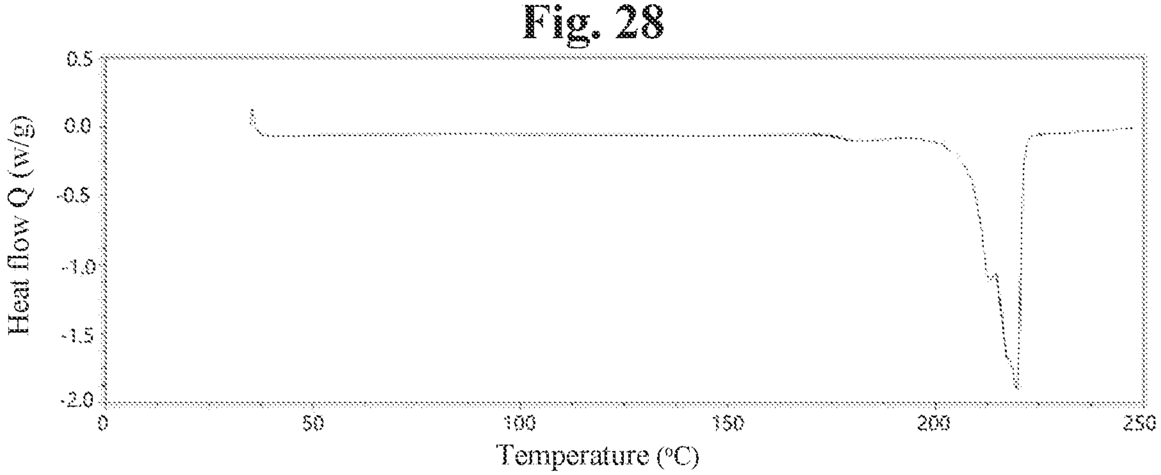
FIG. 29 shows a DSC pattern of the crystal form IV of the compound 1 prepared in Example 14.

In some embodiments, a DSC pattern of the crystal form IV of the compound I is substantially as shown in FIG. 29, and is preferably as shown in FIG. 29.

Figure 30:
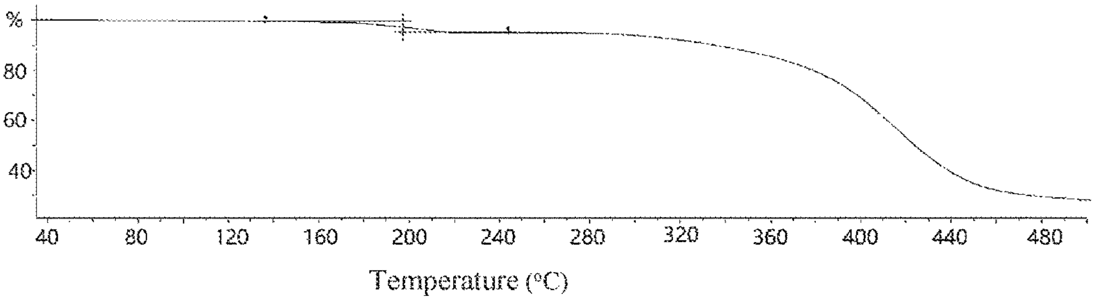
FIG. 30 shows a TGA pattern of the crystal form IV of the compound I prepared in Example 14.

In some embodiments, a TGA pattern of the crystal form IV of the compound I is substantially as shown in FIG. 30, and is preferably as shown in FIG. 30.

Crystal Form V of Compound I

Figure 31:
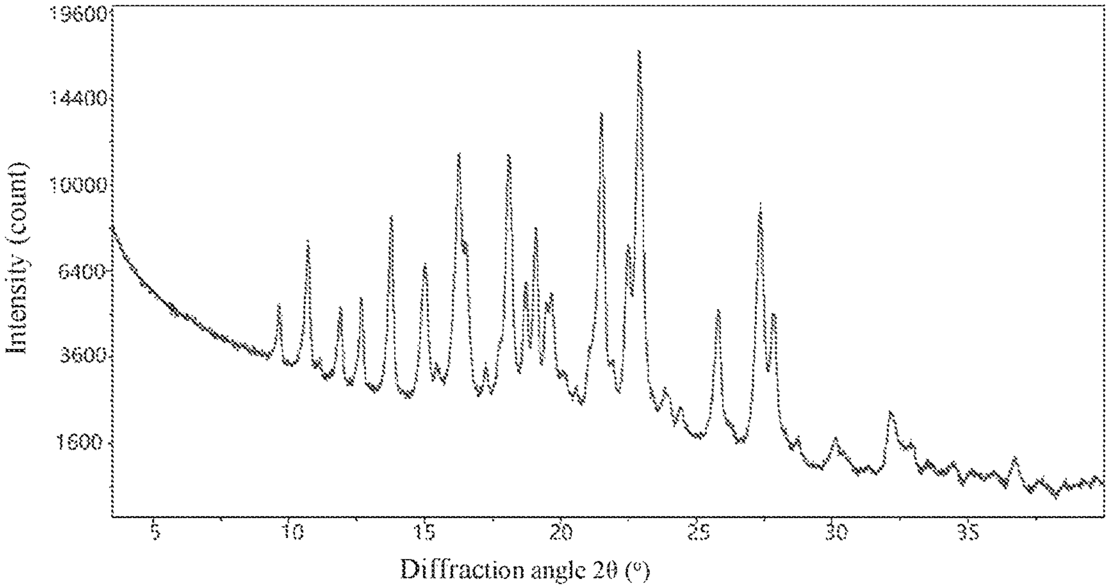
FIG. 31 shows an XRPD pattern of a crystal form V of the compound I prepared in Example 15.

In some embodiments, an XRPD pattern of the crystal form V of the compound I is substantially as shown in FIG. 31, and is preferably as shown in FIG. 31.

Figure 32:
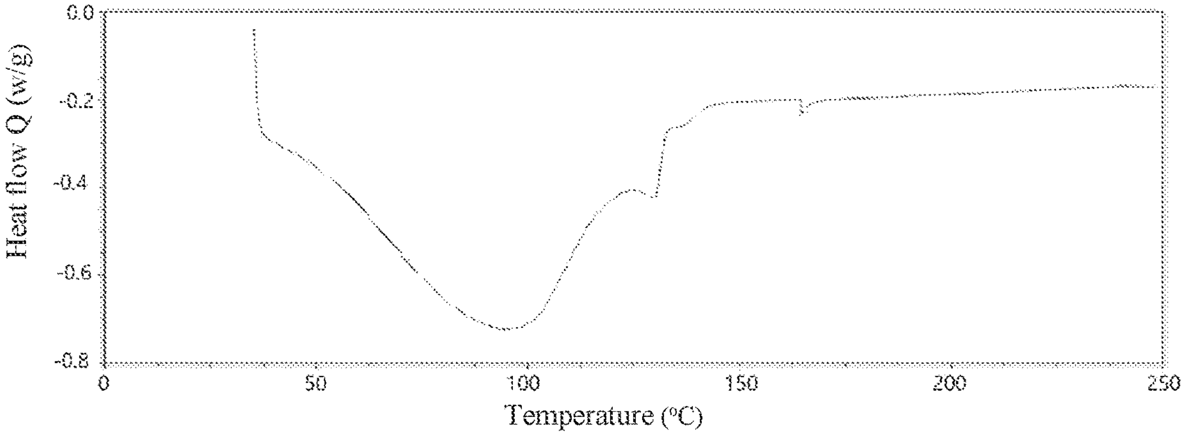
FIG. 32 shows a DSC pattern of the crystal form V of the compound I prepared in Example 15.

In some embodiments, a DSC pattern of the crystal form V of the compound I is substantially as shown in FIG. 32, and is preferably as shown in FIG. 32.

Figure 33:
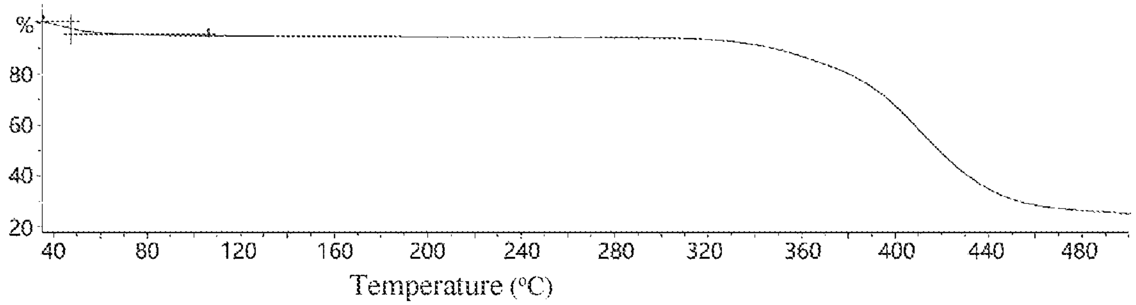
FIG. 33 shows a TGA pattern of the crystal form V of the compound I prepared in Example 15.

In some embodiments, a TGA pattern of the crystal form V of the compound I is substantially as shown in FIG. 33, and is preferably as shown in FIG. 33.

Crystal Form VI of Compound I

In some embodiments, the compound I is the crystal form VI of the compound I, an XRPD pattern of which exhibits at least two, at least three, at least four, at least five, or at least six diffraction angles 2θ (°) at maximum intensity.

In some embodiments, the XRPD pattern of the crystal form VI of the compound I comprises diffraction peaks at 2θ of about 18.04±0.2°, 19.56±0.2°, 22.63±0.2°, and/or 27.24±0.2°. Preferably, the XRPD pattern of the crystal form VI of the compound I further comprises diffraction peaks at 2θ of about 5.53±0.2°, 15.91±0.2°, and/or 18.70±0.2°. More preferably, the XRPD pattern of the crystal form VI of the compound I further comprises diffraction peaks at 2θ of about 14.14±0.2°, 14.88±0.2°, 16.90±0.2°, and/or 20.37±0.2°. Still more preferably, the XRPD pattern of the crystal form VI of the compound I further comprises diffraction peaks at 2θ of about 11.17±0.2°, 12.95±0.2°, 20.89±0.2°, 25.15±0.2°, 26.21±0.2°, 26.93±0.2°, and/or 27.81±0.2°.

Figure 34:
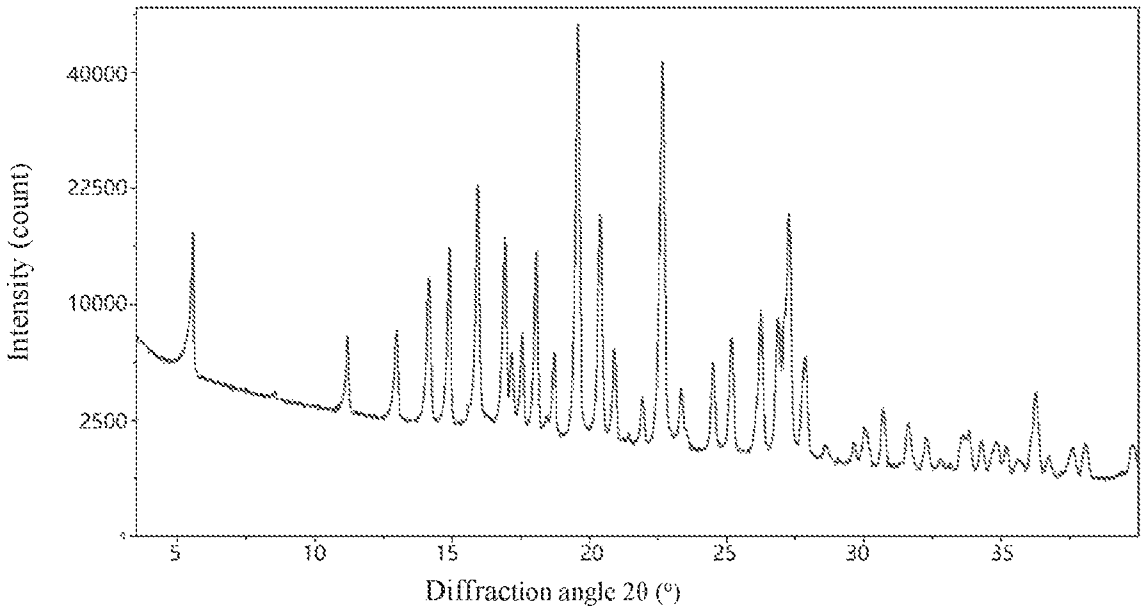
FIG. 34 shows an XRPD pattern of a crystal form VI of the compound I prepared in Example 16.

In some embodiments, the XRPD pattern of the crystal form VI of the compound I is substantially as shown in FIG. 34, and is preferably as shown in FIG. 34.

Figure 35:
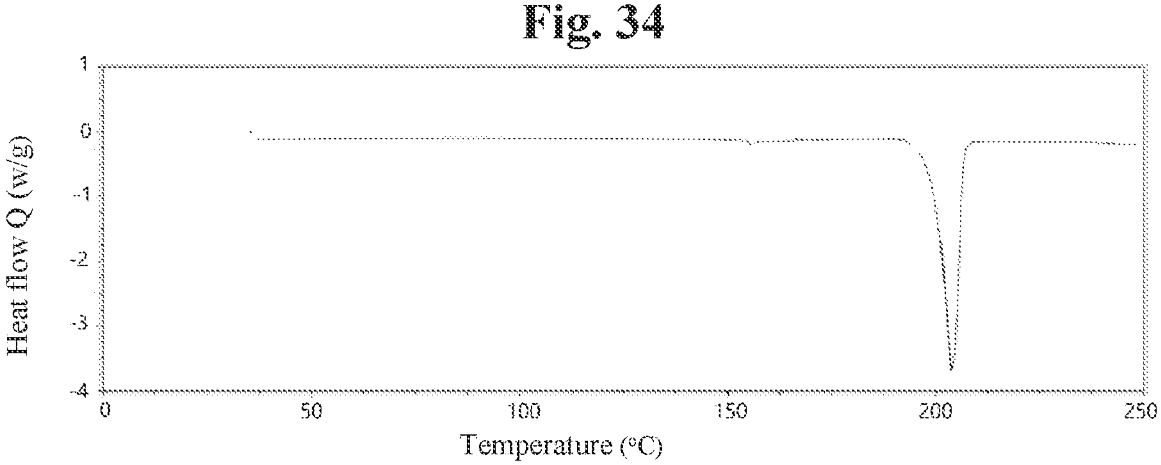
FIG. 35 shows a DSC pattern of the crystal form VI of the compound I prepared in Example 16.

In some embodiments, an onset temperature of an endothermic peak of the crystal form VI of the compound I is about 199.5° C.±5° C., and is preferably about 199.5° C.±2° C. More preferably, a DSC pattern of the crystal form VI of the compound I is substantially as shown in FIG. 35, and is preferably as shown in FIG. 35.

Figure 36:
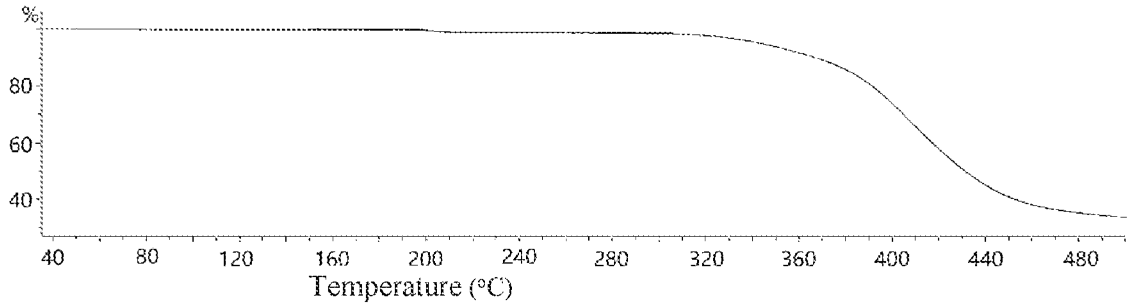
FIG. 36 shows a TGA pattern of the crystal form VI of the compound 1 prepared in Example 16.

In some embodiments, a TGA pattern of the crystal form VI of the compound I is substantially as shown in FIG. 36, and is preferably as shown in FIG. 36.

In some embodiments, the crystal form VI of the compound I is an anhydrate.

Methods for Preparing Crystal Forms

For the compound I and salts thereof of the present invention, the formation of various crystal forms depends to some extent on the choice of particular solvents or solvent combination, and the method of combining solvents may also affect the formation of crystal forms. Solvents usable for preparing the various crystal forms of the present invention include, but are not limited to, for example, water, methanol, ethanol, isopropanol, tetrahydrofuran, 2-methyltetrahydrofuran, acetonitrile, ethyl acetate, N,N-dimethylformamide, and any mixture thereof.

The presence of impurities may affect the formation of one crystalline form of a compound in favor of another crystalline form of the compound. Therefore, for a salt (e.g., the fumarate salt) of the compound I of the present invention, in a salt forming reaction between the compound I and an acid (e.g., fumaric acid), the presence of impurities in the system has an impact on the formed specific crystal form.

The present invention provides a method for preparing one or more of the above crystal forms of the compound I or the salts thereof.

In some embodiments, a method for preparing a crystal form A of the fumarate salt of the compound I is provided, including reacting the compound I with fumaric acid in a solvent, and then separating the resulting solid, where said solvent is methanol, tetrahydrofuran, or 2-methyltetrahydrofuran. Preferably, said reaction is carried out at an elevated temperature (e.g., about 40-70° C., preferably about 50-60° C., e.g., about 55° C.).

In some embodiments, a method for preparing a crystal form A of the fumarate salt of the compound I is provided, including adding a solvent into the compound I, then adding fumaric acid for reaction, and then separating the resulting solid, where said solvent is methanol, tetrahydrofuran, or 2-methyltetrahydrofuran.

In some embodiments, a method for preparing a crystal form B of the fumarate salt of the compound I is provided, including reacting the compound I with fumaric acid in a solvent, and then separating the resulting solid, where said solvent is methanol. Preferably, the reaction is carried out at an elevated temperature (e.g., about 40-70° C., preferably about 50-60° C., e.g., about 55° C.).

In some embodiments, a method for preparing a crystal form B of the fumarate salt of the compound I is provided, including adding a solvent into fumaric acid, then adding the compound I for reaction, and then separating the resulting solid, where said solvent is methanol.

In some embodiments, a method for preparing a crystal form C of the fumarate salt of the compound I is provided, including mixing the fumarate salt (the crystal form A of the fumarate salt or the crystal form B of the fumarate salt) of the compound I with a solvent, then stirring, and separating the resulting solid, where said solvent is a mixture of ethanol and water. Preferably, stirring is lasted for a duration enough for the conversion of the crystal form A or the crystal form B into the crystal form C for, e.g., from 1 to 5 days, preferably from 2 to 4 days, such as 3 days (72 h), and stirring may be carried out at room temperature.

In some embodiments, a method for preparing a crystal form D of the fumarate salt of the compound I is provided, including mixing the fumarate salt (e.g., the crystal form A of the fumarate salt) of the compound I with a solvent, then stirring, and separating the resulting solid, where said solvent is N,N-dimethylformamide. Preferably, stirring is lasted for a duration enough for the conversion of the crystal form A into the crystal form D for, e.g., from 1 to 5 days, preferably from 2 to 4 days, such as 3 days (72 h), and stirring may be carried out at a temperature from 20 to 40° C. (e.g., 20° C., 30° C., or 40° C.).

In some embodiments, a method for preparing a crystal form F of the fumarate salt of the compound I is provided, including mixing the fumarate salt (e.g., the crystal form A of the fumarate salt) of the compound I with a solvent, then adding a poor solvent dropwise, and separating the resulting solid, where said solvent is N,N-dimethylformamide, and the poor solvent is water.

In some embodiments, a method for preparing a crystal form G of the fumarate salt of the compound I is provided, including mixing the fumarate salt (e.g., the crystal form F of the fumarate salt) of the compound I with a solvent, then stirring, and separating the resulting solid, where said solvent is n-heptane. Preferably, stirring is lasted for a duration enough for the conversion of the crystal form F into the crystal form G for, e.g., from 1 to 5 days, preferably from 2 to 4 days, such as 3 days (72 h), and stirring may be carried out at a temperature from 20 to 40° C. (e.g., 20° C., 30° C., or 40° C.).

In some embodiments, a method for preparing a crystal form A of a p-toluenesulfonate salt of the compound 1 is provided, including reacting the compound I with p-toluenesulfonic acid in a solvent, and then separating the resulting solid, where said solvent is acetonitrile. Preferably, the reaction is carried out at room temperature or at an elevated temperature (e.g., about 20-45° C.).

In some embodiments, a method for preparing a crystal form I of the compound I is provided, including mixing the compound I with a solvent, then stirring, and separating the resulting solid, where said solvent is ethyl acetate. Preferably, stirring is lasted for a duration enough for the production of the crystal form I for, e.g., from 1 to 5 days, preferably from 2 to 4 days, such as 3 days (72 h), and stirring may be carried out at room temperature.

In some embodiments, a method for preparing a crystal form II of the compound I is provided, including mixing a crystal form (e.g., the crystal form I) of the compound I with a solvent, then stirring, and separating the resulting solid, where said solvent is N,N-dimethylformamide. Preferably, stirring is lasted for a duration enough for the conversion of the crystal form I into the crystal form II for, e.g., from 1 to 5 days, preferably from 2 to 4 days, such as 3 days (72 h), and stirring may be carried out at a temperature from 20 to 40° C. (e.g., 20° C., 30° C., or 40° C.).

In some embodiments, a method for preparing a crystal form III of the compound I is provided, including mixing the compound I with a solvent, then stirring, and separating the resulting solid, where said solvent is n-propanol. Preferably, stirring is lasted for a duration enough for the production of the crystal form III for, e.g., from 1 to 5 days, preferably from 2 to 4 days, such as 3 days (72 h), and stirring may be carried out at room temperature.

In some embodiments, a method for preparing a crystal form IV of the compound I is provided, including mixing the compound I with a solvent, then stirring, and separating the resulting solid, where said solvent is dichloromethane. Preferably, stirring is lasted for a duration enough for the production of the crystal form IV for, e.g., from 1 to 5 days, preferably from 2 to 4 days, such as 3 days (72 h), and stirring may be carried out at room temperature.

In some embodiments, a method for preparing a crystal form V of the compound I is provided, including mixing the compound I with a solvent, then stirring, and separating the resulting solid, where said solvent is acetonitrile. Preferably, stirring is lasted for a duration enough for the production of the crystal form V for, e.g., from 1 to 5 days, preferably from 2 to 4 days, such as 3 days (72 h), and stirring may be carried out at room temperature.

In some embodiments, a method for preparing a crystal form VI of the compound I is provided, including mixing the compound I with a solvent, then allowing the mixture to stand at room temperature, and separating the resulting solid, where said solvent is methanol. Preferably, the mixture is kept at room temperature for a duration enough for the production of the crystal form VI for, e.g., from 1 h to 5 days, such as 5 h, 10 h, 1 day, 3 days, and 5 days.

The present invention will be further elaborated below with reference to examples, which are only intended to illustrate the present invention for better understanding, but are not intended to limit the scope of the present invention.

Characterization of Crystalline Forms

The various crystal forms or amorphous forms prepared in the Examples are characterized by X-ray powder diffraction (XRPD), differential scanning calorimetry (DSC), thermogravimetric analysis (TGA), and nuclear magnetic resonance (NMR) spectroscopy.

Characterization Method:

(1) XRPD

The XRPD patterns of the various crystal forms are collected on an X-ray powder diffraction analyzer (PANalytacal X'Pert3 Powder) in a transmission mode. A 2θ scanning range is from 3.5° to 40° (Cu Kα emitter at a wavelength of 1.5206 Å) at a scanning current of 40 mA and a scanning voltage of 40 KV. Continuous transmission scanning is performed using Absolute scan at room temperature at a step length of 0.013° with residence time of 50 s.

(2) DSC

The DSC patterns of the various crystal forms are collected using a TA DSC2500 differential scanning calorimeter. The test temperature range is from 35° C. to 250° C., and the heating rate is 10° C./min. During the test, nitrogen is purged at a flow rate of 50 mL/min.

(3) TGA

The TGA patterns of the various crystal forms are collected using METTLER TOLEDO TGA 1. The test temperature range is from 35° C. to 500° C., and the heating rate is 10° C./min. During the test, nitrogen is purged at a flow rate of 50 mL/min.

(4) Nuclear Magnetic Resonance (NMR) Spectroscopy

A Bruker superconducting nuclear magnetic resonance spectrometer (model AVACE III HD 400 MHz) is employed for $^1$H NMR.

EXAMPLES

Example 1: Preparation of 2-(6-(6-((6-(4-fluoro-1H-pyrazol-1-yl)pyridin-3-yl)methyl)-3,6-diazabicyclo[3.1.1]heptan-3-yl)pyridin-3-yl)-6-methyl-N-(5-methyl-1H-pyrazol-3-yl)pyrimidin-4-amine (Compound 1)

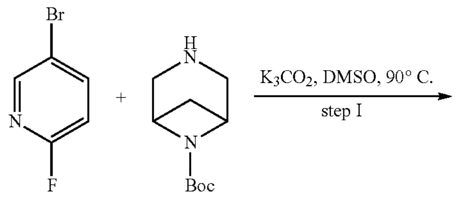

1a 1b

-continued

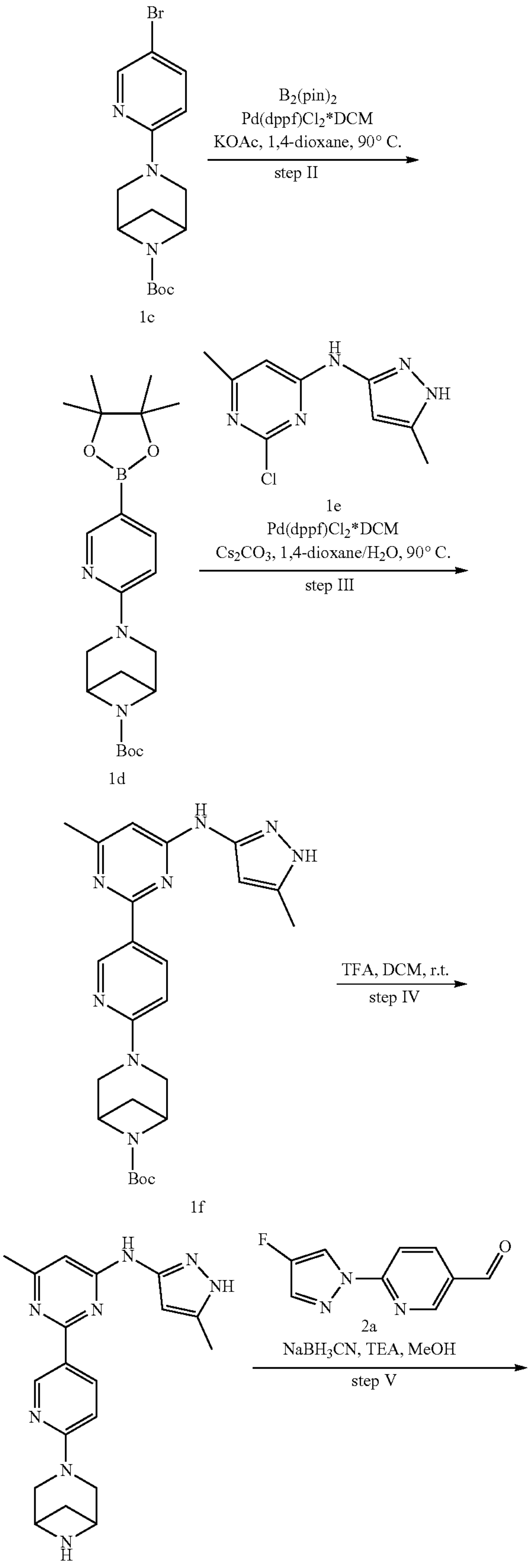

1c 1d 1f 1g

-continued

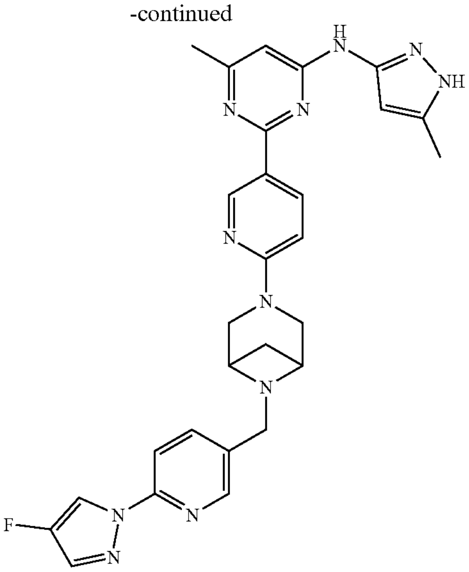

I

Step I: Preparation of tert-butyl 3-(5-bromopyridin-2-yl)-3,6-diazabicyclo[3.1.1]heptane-6-carboxylate (Compound 1c)

A compound 1a (1.50 g) and a compound 1b (1.77 g) were successively added into a 100 mL single-necked flask, and then DMSO (20.0 mL) and $K_2CO_3$ (5.83 g) were successively added. The mixture was heated to 90° C. and stirred under the protection of nitrogen for 20 h. After the reaction was complete, the reaction liquid was cooled to room temperature, added with water (100 mL) for diluting, and extracted with EA. The organic phases were combined, washed with saturated brine, dried over anhydrous sodium sulfate, filtered, concentrated under reduced pressure, and separated and purified by flash column chromatography on silica gel (PE:EA=5:1), to provide the compound 1c (2.03 g). MS m/z (ESI): 354.1 $[M+H]^+$.

Step II: Preparation of tert-butyl 3-(5-(4,4,5,5-tetramethyl-1,3,2-dioxaborolan-2-yl)pyridin-2-yl)-3,6-diazabicyclo[3.1.1]heptane-6-carboxylate (Compound 1d)

The compound 1c (2.03 g), $B_2(pin)_2$ (4.01 g), KOAc (1.55 g), 1,4-dioxane (15.0 mL), and Pd(dppf)$Cl_2$·DCM (644.67 mg) were successively added into a 100 mL single-necked flask, and were heated to 90° C. for reaction under the protection of nitrogen. After the reaction was complete, the reaction liquid was cooled to room temperature, added with water (30 mL) for diluting, and extracted with EA (40 mL×3). The organic phases were combined, washed with saturated brine, dried over anhydrous sodium sulfate, filtered, concentrated to dryness under reduced pressure, and separated and purified by flash column chromatography on silica gel (DCM:MeOH=15:1), to provide the compound 1d (2.11 g). MS m/z (ESI): 402.3 $[M+H]^+$.

Step III: Preparation of tert-butyl 3-(5-(4-methyl-6-((5-methyl-1H-pyrazol-3-yl)amino)pyrimidin-2-yl)pyridin-2-yl)-3,6-diazabicyclo[3.1.1]heptane-6-carboxylate (Compound 1f)

A compound 1e (950 mg) was dissolved in 1,4-dioxane (50.0 mL), the compound 1d (2.11 g), $Cs_2CO_3$ (3.15 g), and water (5.0 mL) were successively added, and then Pd(dppf)$Cl_2$·DCM (477.83 mg) was added. The mixture was heated to 90° C. for reaction under the protection of nitrogen for 14 h. After the reaction was complete, the reaction liquid was cooled to room temperature, added with water (100 mL) for diluting, and extracted with EA (60 mL×3). The organic phases were combined, washed with saturated brine, dried over anhydrous sodium sulfate, filtered, and then concentrated to dryness under reduced pressure, to provide the compound 1f (587.0 mg). MS m/z (ESI): 463.3 $[M+H]^+$.

Step V: Preparation of 2-(6-(3,6-diazabicyclo[3.1.1]heptan-3-yl)pyridin-3-yl)-6-methyl-N-(5-methyl-1H-pyrazol-3-yl)pyrimidin-4-amine (Compound 1g)

The compound 1f (1.36 g) was dissolved in DCM (20.0 mL), and then TFA (20.0 mL) was added. The mixture was kept at room temperature for reaction under the protection of nitrogen. After the reaction was complete, the reaction liquid was concentrated to dryness under reduced pressure, and separated and purified by Prep-HPLC to provide a trifluoroacetate salt of the compound 1g (587.0 mg). MS m/z (ESI): 363.3 $[M+H]^+$.

Step V: Preparation of 2-(6-(6-((6-(4-fluoro-1H-pyrazol-1-yl)pyridin-3-yl)methyl)-3,6-diazabicyclo[3.1.1]heptan-3-yl)pyridin-3-yl)-6-methyl-N-(5-methyl-1H-pyrazol-3-yl)pyrimidin-4-amine (Compound 1)

The trifluoroacetate salt of the compound 1g (22.82 mg) and a compound 2a (27.47 mg) were added into methanol (1.0 mL), and then triethylamine (4.45 mg) and sodium cyanoborohydride (13.86 mg) were successively added. The mixture was kept at room temperature for reaction for 14 h. After the reaction was complete, the reaction liquid was concentrated to dryness under reduced pressure, and separated and purified by Prep-HPLC to provide the compound I (7.0 mg), which is an amorphous form. MS m/z (ESI): 538.3 $[M+H]^+$.

$^1$H NMR (400 MHz, DMSO-$d_6$) δ 11.98 (s, 1H), 9.66 (s, 1H), 9.12 (d, J=2.16 Hz, 1H), 8.67 (dd, J=4.54, 0.64 Hz, 1H), 8.43 (dd, J=8.94, 2.28 Hz, 1H), 8.41 (d, J=1.68 Hz, 1H), 7.98 (dd, J=8.48, 2.12 Hz, 1H), 7.92 (d, J=4.28 Hz, 1H), 7.87 (d, J=8.4 Hz, 1H), 6.78 (d, J=9.0 Hz, 2H), 6.31 (br, 1H), 3.78-3.71 (m, 4H), 3.68-3.52 (m, 4H), 2.59-2.52 (m, 1H), 2.33 (s, 3H), 2.25 (s, 3H), 1.60 (d, J=8.36 Hz, 1H).

Example 2: Preparation of Crystal Form A of Fumarate Salt of Compound 1

Method 1: The compound I (10.0 g) prepared in Example 1 was added into a glass bottle, 200 mL of tetrahydrofuran was added, and the mixture was warmed to a temperature of 55° C. Fumaric acid (2.59 g) was added. The mixture was maintained at a temperature of 55° C. for reaction, and then filtered to provide the crystal form A of the fumarate salt of the compound I.

An XRPD pattern of the crystal form A of the fumarate salt of the resulting compound I is as shown in FIG. 1, and XRPD peak positions and relative peak intensities are provided in Table 1.

TABLE 1

XRPD Data of Crystal Form A of Fumarate Salt of Compound I

| Peak position 2θ (°) ± 0.2° | Relative peak intensity % |
|---|---|
| 5.44 | 83.37 |
| 9.75 | 85.80 |
| 10.99 | 22.04 |
| 12.09 | 20.83 |
| 12.84 | 9.43 |
| 13.89 | 24.59 |
| 14.87 | 20.39 |
| 15.63 | 14.62 |
| 16.25 | 29.08 |
| 16.56 | 5.63 |
| 16.74 | 7.24 |
| 17.02 | 6.50 |
| 17.28 | 45.28 |
| 18.13 | 32.62 |
| 18.43 | 100 |
| 19.11 | 23.95 |
| 19.70 | 5.48 |
| 20.48 | 11.29 |
| 21.08 | 8.59 |
| 21.55 | 15.84 |
| 22.14 | 10.17 |
| 22.55 | 17.59 |
| 23.56 | 19.02 |
| 23.83 | 15.34 |
| 25.64 | 5.69 |
| 26.55 | 44.41 |
| 27.86 | 48.57 |
| 29.86 | 14.64 |

Method 2: The compound 1 (10.0 g) prepared in Example 1 was added into a glass bottle, 200 mL of methanol was added, and the mixture was warmed to a temperature of 55° C. Amorphous powder of the compound I as a seed crystal was added, and fumaric acid (2.59 g) was added. The mixture was maintained at a temperature of 55° C. for reaction, and then filtered to provide the crystal form A of the fumarate salt of the compound I.

Method 3: The compound I (10.0 g) prepared in Example 1 was added into a glass bottle, 200 mL of 2-methyltetrahydrofuran was added, and the mixture was warmed to a temperature of 55° C. Fumaric acid (2.59 g) was added. The mixture was maintained at a temperature of 55° C. for reaction, and then filtered to provide the crystal form A of the fumarate salt of the compound 1.

An XRPD pattern of the crystal form A of the fumarate salt of the compound I prepared in Method 2 and Method 3 is substantially as shown in FIG. 1.

Example 3: Preparation of Crystal Form B of Fumarate Salt of Compound I

Fumaric acid (3.24 g) was added into a glass bottle, 200 mL of methanol was added, and the mixture was warmed to a temperature of 55° C. The compound 1 (10.0 g) prepared in Example 1 was added portionwise. The mixture was maintained at a temperature of 55° C. for reaction, and then filtered to provide the crystal form B of the fumarate salt of the compound 1.

An XRPD pattern of the crystal form B of the fumarate salt of the resulting compound I is as shown in FIG. 4, and XRPD peak positions and relative peak intensities are provided in Table 2.

A DSC pattern of the crystal form B of the fumarate salt of the resulting compound I is as shown in FIG. 5, and an onset temperature of an endothermic peak of a sample is about 202.21° C.±2° C.

TABLE 2

XRPD Data of Crystal Form B of Fumarate Salt of Compound I

| Peak position 2θ (°) ± 0.2° | Relative peak intensity % |
|---|---|
| 5.70 | 7.35 |
| 9.12 | 41.36 |
| 11.50 | 6.01 |
| 13.62 | 11.46 |
| 15.29 | 13.27 |
| 15.64 | 28.68 |
| 16.26 | 7.99 |
| 16.57 | 100 |
| 17.31 | 6.56 |
| 18.05 | 23.39 |
| 19.64 | 8.77 |
| 21.13 | 26.57 |
| 21.81 | 12.36 |
| 22.08 | 24.69 |
| 23.87 | 9.20 |
| 24.78 | 47.46 |
| 25.58 | 12.04 |
| 25.74 | 40.76 |
| 26.91 | 18.07 |
| 27.24 | 5.32 |

Example 4: Preparation of Crystal Form C of Fumarate Salt of Compound I

Method 1: The crystal form A (200 mg) of the fumarate salt of the compound I was added into a glass bottle. 4 mL of ethanol and 2 mL of water were added. The mixture was stirred at room temperature for 72 h, and then filtered to provide the crystal form C of the fumarate salt of the compound 1.

An XRPD pattern of the crystal form C of the fumarate salt of the resulting compound I is as shown in FIG. 6, and XRPD peak positions and relative peak intensities are provided in Table 3.

TABLE 3

XRPD Data of Crystal Form C of Fumarate Salt of Compound I

| Peak position 2θ (°) ± 0.2° | Relative peak intensity % |
|---|---|
| 8.58 | 5.22 |
| 9.13 | 100 |
| 10.05 | 10.18 |
| 11.09 | 20.52 |
| 13.27 | 13.56 |
| 13.78 | 11.43 |
| 14.39 | 14.19 |
| 16.84 | 5.47 |
| 17.24 | 10.25 |
| 17.63 | 30.57 |
| 18.08 | 22.74 |
| 20.21 | 30.36 |
| 22.31 | 32.77 |
| 23.12 | 7.20 |
| 25.13 | 8.42 |
| 26.08 | 75.92 |
| 27.92 | 26.10 |

Method 2: The crystal form B (200 mg) of the fumarate salt of the compound I was added into a glass bottle. 4 mL of ethanol and 2 mL of water were added. The mixture was stirred at room temperature for 72 h, and then filtered to provide the crystal form C of the fumarate salt of the compound I. An XPRD pattern of the crystal form C of the fumarate salt of the resulting compound I is substantially as shown in FIG. 6.

Example 5: Preparation of Crystal Form A of p-Toluenesulfonate Salt of Compound I The compound I (50 mg) prepared in Example 1 was added into a glass bottle. 2 mL of acetonitrile and p-toluenesulfonic acid (37.2 mg) were added. The mixture was stirred at 20-45° C. for 48 h, and then filtered to provide the crystal form A of the p-toluenesulfonate salt of the compound I.

An XRPD pattern of the crystal form A of the p-toluenesulfonate salt of the compound I is as shown in FIG. 7, and XRPD peak positions and relative peak intensities are provided in Table 4.

A DSC pattern of the crystal form A of the p-toluenesulfonate salt of the compound I is as shown in FIG. 8, and an onset temperature of an endothermic peak of a sample is about 43.71° C. 2° C.

A TGA pattern of the crystal form A of the p-toluenesulfonate salt of the compound I is as shown in FIG. 9, and the crystal form is an anhydrate.

TABLE 4

XRPD Data of Crystal Form A of p-Toluenesulfonate Salt of Compound I

| Peak position 2θ (°) ± 0.2° | Relative peak intensity % |
|---|---|
| 4.69 | 100 |
| 8.25 | 12.47 |
| 10.65 | 8.47 |
| 12.23 | 12.01 |
| 12.77 | 8.52 |
| 13.87 | 54.84 |
| 15.60 | 19.16 |
| 16.98 | 21.80 |
| 17.83 | 10.16 |
| 18.23 | 25.54 |
| 19.27 | 28.69 |
| 19.98 | 20.75 |
| 20.84 | 7.13 |
| 22.08 | 26.63 |
| 22.49 | 14.48 |
| 23.35 | 27.75 |
| 24.30 | 14.76 |
| 25.17 | 14.76 |
| 25.78 | 20.58 |
| 28.13 | 11.45 |

Example 6: Preparation of Crystal Form I of Compound I

The compound I (1.0 g) prepared in Example 1 was added into a glass bottle. 20 mL of ethyl acetate was added. The mixture was stirred at room temperature for 72 h, and then filtered to provide the crystal form I of the compound I.

An XRPD pattern of the crystal form I of the compound I is as shown in FIG. 10, and XRPD peak positions and relative peak intensities are provided in Table 5.

A DSC pattern of the crystal form I of the compound I is as shown in FIG. 11, and an onset temperature of an endothermic peak of a sample is about 190.79° C.±2° C.

A TGA pattern of the crystal form I of the compound I is as shown in FIG. 12, and the crystal form is an anhydrate.

TABLE 5

XRPD Data of Crystal Form I of Compound I

| Peak position 2θ (°) ± 0.2° | Relative peak intensity % |
|---|---|
| 5.53 | 53.21 |
| 11.18 | 19.97 |
| 12.33 | 11.89 |
| 12.67 | 18.65 |
| 12.95 | 16.44 |
| 14.12 | 28.79 |
| 14.46 | 19.47 |
| 14.89 | 29.30 |
| 15.95 | 46.82 |
| 16.89 | 37.45 |
| 18.00 | 83.32 |
| 18.36 | 17.14 |
| 18.77 | 48.60 |
| 19.55 | 98.51 |
| 20.13 | 21.64 |
| 20.36 | 38.00 |
| 20.87 | 10.37 |
| 21.71 | 34.19 |
| 22.62 | 100 |
| 24.86 | 32.95 |
| 25.13 | 15.89 |
| 25.67 | 20.43 |
| 26.16 | 18.58 |
| 26.84 | 15.59 |
| 27.20 | 73.92 |
| 27.80 | 11.02 |
| 28.28 | 15.27 |

Example 7: Preparation of Crystal Form A of Fumarate Salt of Compound I

The crystal form C (6 g) of the fumarate salt of the compound I was stirred in anhydrous ethanol at 45° C. for more than 12 h to provide a crystal of the fumarate salt of the compound I. The crystal is characterized by nuclear magnetic resonance spectroscopy, and the $^1$H NMR data is as follows.

$^1$H NMR (400 MHz, DMSO-$d_6$) δ 12.68 (br, 3H), 9.65 (s, 1H), 9.13 (d, J=2.0 Hz, 1H), 8.66 (d, J=4.4 Hz, 1H), 8.44 (dd, J=8.8, 2.0 Hz, 1H), 8.41 (d, J=1.2 Hz, 1H), 7.97 (dd, J=8.4, 1.6 Hz, 1H), 7.91 (d, J=4.4 Hz, 1H), 7.86 (d, J=8.4 Hz, 1H), 6.81 (br, 1H), 6.77 (d, J=8.8 Hz, 1H), 6.62 (s, 2H), 6.30 (br, 1H), 3.79-3.76 (m, 4H), 3.67-3.60 (m, 4H), 2.62-2.56 (m, 1H), 2.33 (s, 3H), 2.25 (s, 3H), 1.61 (d, J=8.4 Hz, 1H).

An XRPD pattern of the resulting crystal is as shown in FIG. 2, and XRPD peak positions and relative peak intensities are provided in Table 6. As can be seen from XRPD data, the resulting crystal is the crystal form A of the fumarate salt of the compound 1.

A DSC pattern is as shown in FIG. 3A, and an onset temperature of an endothermic peak of a sample is about 206.5° C.±2° C.

A TGA pattern s as shown in FIG. 3B, and the crystal form is an anhydrate.

TABLE 6

XRPD Data of Crystal Form A of Fumarate Salt of Compound I

| Peak position 2θ (°) ± 0.2° | Relative peak intensity % |
|---|---|
| 5.46 | 70.94 |
| 9.77 | 58.73 |
| 11.00 | 17.31 |

TABLE 6-continued

XRPD Data of Crystal Form A of Fumarate Salt of Compound I

| Peak position 2θ (°) ± 0.2° | Relative peak intensity % |
|---|---|
| 12.10 | 14.26 |
| 12.83 | 8.91 |
| 13.89 | 31.42 |
| 14.86 | 19.53 |
| 15.63 | 18.15 |
| 16.26 | 23.75 |
| 16.49 | 4.98 |
| 16.73 | 10.77 |
| 17.02 | 9.34 |
| 17.22 | 57.3 |
| 18.05 | 37.8 |
| 18.42 | 100 |
| 19.08 | 31.35 |
| 19.72 | 6.3 |
| 20.45 | 19.22 |
| 21.02 | 12.96 |
| 21.48 | 23.5 |
| 22.17 | 6.85 |
| 22.50 | 23.04 |
| 23.51 | 25.21 |
| 23.80 | 17.07 |
| 25.66 | 3.47 |
| 26.44 | 65.34 |
| 27.75 | 62.5 |
| 29.81 | 20.43 |

Example 8: Preparation of Crystal Form D of Fumarate Salt of Compound I

The crystal form A (about 200 mg) of the fumarate salt of the compound I was suspended by stirring in DMF (about 1 mL) at 20° C. or 40° C. for 72 h to provide the crystal form D of the fumarate salt of the compound I. An XRPD pattern of the resulting crystal form D is as shown in FIG. 13, and XRPD peak positions and relative peak intensities are provided in Table 7. A DSC pattern is as shown in FIG. 14, and an onset temperature of an endothermic peak of a sample is about 159.0° C.±2° C. As can be seen from a TGA pattern shown in FIG. 15, when the sample was heated to 180° C., the weight loss was about 11%.

TABLE 7

XRPD Data of Crystal Form D of Fumarate Salt of Compound I

| Peak position 2θ (°) ± 0.2° | Relative peak intensity % |
|---|---|
| 4.66 | 25.17 |
| 5.40 | 6.53 |
| 9.43 | 63.87 |
| 10.56 | 16.79 |
| 12.21 | 23.45 |
| 13.0 | 5.21 |
| 14.2 | 13.7 |
| 14.5 | 12.03 |
| 15.21 | 30.76 |
| 15.70 | 57.92 |
| 16.19 | 12.13 |
| 16.5 | 60.99 |
| 16.97 | 69.99 |
| 17.74 | 100 |
| 18.23 | 89.66 |
| 18.59 | 21.18 |
| 18.90 | 36.86 |
| 19.28 | 8.39 |
| 19.72 | 9.52 |
| 20.54 | 79.5 |
| 21.12 | 17.1 |

TABLE 7-continued

XRPD Data of Crystal Form D of Fumarate Salt of Compound I

| Peak position 2θ (°) ± 0.2° | Relative peak intensity % |
|---|---|
| 21.4 | 35.25 |
| 22.41 | 44.55 |
| 23.30 | 30.65 |
| 23.59 | 44.94 |
| 23.83 | 53.09 |
| 24.26 | 8.56 |
| 24.69 | 7.28 |
| 25.16 | 15.11 |
| 25.57 | 9.02 |
| 25.87 | 9.42 |
| 27.03 | 41.64 |
| 27.69 | 5.79 |
| 29.09 | 5.91 |
| 29.44 | 15.25 |

Example 9: Preparation of Crystal Form F of Fumarate Salt of Compound I

The crystal form A (4.0 g) of the fumarate salt of the compound I was dissolved in hot DMF (60 ml), and 140 mL of purified water was added. After a seed crystal of the crystal form F of the fumarate salt of the compound I was added (1.5 mL of water was added into 500 μL of a solution of about 100 mg/mL fumarate salt of the compound I to separate out the seed crystal of the crystal form F), 40 mL of purified water was added dropwise. The solid was filtered and dried to provide the crystal form F (2.67 g) of the fumarate salt of the compound 1. An XRPD pattern of the resulting crystal form F is as shown in FIG. 16, and XRPD peak positions and relative peak intensities are provided in Table 8. A DSC pattern is as shown in FIG. 17, and has a broad endothermic peak at 40-150'° C. As can be seen from a TGA pattern shown in FIG. 18, when a sample was heated to 100° C., the weight loss was about 10%.

TABLE 8

XRPD Data of Crystal Form F of Fumarate Salt of Compound I

| Peak position 2θ (°) ± 0.2° | Relative peak intensity % |
|---|---|
| 5.96 | 100 |
| 8.75 | 5.37 |
| 9.03 | 8.28 |
| 12.03 | 8.51 |
| 12.85 | 19.56 |
| 13.86 | 20.83 |
| 15.70 | 9.49 |
| 16.05 | 9.81 |
| 16.34 | 7.78 |
| 17.17 | 23.56 |
| 18.15 | 34.58 |
| 20.76 | 19.58 |
| 21.71 | 9.52 |
| 21.90 | 10.36 |
| 23.61 | 9.6 |
| 25.42 | 17.12 |
| 25.76 | 46.6 |
| 26.48 | 49.86 |
| 27.02 | 27.21 |
| 27.49 | 8.57 |
| 28.06 | 9.9 |

Example 10: Preparation of Crystal Form G of Fumarate Salt of Compound I

The crystal form F (about 100 mg) of the fumarate salt of the compound I was suspended by stirring in 1 mL of n-heptane at 40° C. for 72 h. The resulting solid was filtered and dried to provide the crystal form G of the fumarate salt of the compound I. An XRPD pattern of the resulting crystal form G is as shown in FIG. 19, and XRPD peak positions and relative peak intensities are provided in Table 9. A DSC pattern is as shown in FIG. 20, and has a broad endothermic peak at 40-140° C. As can be seen from a TGA pattern shown in FIG. 21, when a sample was heated to 100° C., the weight loss was about 10%.

TABLE 9

XRPD Data of Crystal Form G of Fumarate Salt of Compound I

| Peak position 2θ (°) ± 0.2° | Relative peak intensity % |
|---|---|
| 6.23 | 100 |
| 8.87 | 5.78 |
| 11.34 | 11.22 |
| 11.99 | 5.16 |
| 12.89 | 12 |
| 13.24 | 22.76 |
| 14.87 | 37.65 |
| 15.07 | 7.52 |
| 15.73 | 7.37 |
| 16.45 | 24.25 |
| 16.71 | 10.37 |
| 17.06 | 8.71 |
| 17.34 | 18.71 |
| 17.70 | 13.01 |
| 18.04 | 12.15 |
| 18.36 | 36.43 |
| 19.62 | 21.21 |
| 20.75 | 13.71 |
| 21.56 | 11.28 |
| 21.88 | 9.75 |
| 23.61 | 6.7 |
| 23.84 | 11.28 |
| 24.20 | 5.96 |
| 24.55 | 7.03 |
| 25.31 | 34.68 |
| 26.01 | 39.33 |
| 26.79 | 27.71 |
| 27.22 | 20.58 |
| 27.72 | 11.94 |
| 29.54 | 5.33 |

Example 11: Preparation of Amorphous Form of Compound I

Figure 37:
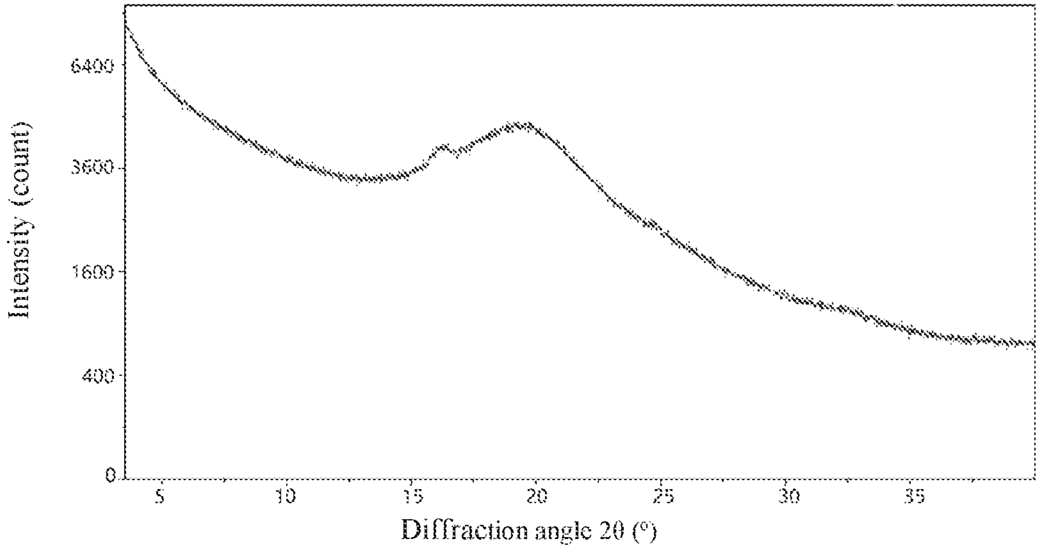
FIG. 37 shows an XRPD pattern of an amorphous form of the compound I prepared in Example 11.

A crystal form I (3.3 g) of the compound I was dissolved in tetrahydrofuran (100 mL), and the solvent was rapidly removed on a rotary evaporator at 50° C. to provide the amorphous form of the compound L. An XRPD pattern of the resulting amorphous form is as shown in FIG. 37.

Example 12: Preparation of Crystal Form II of Compound I

A crystal form I (about 100 mg) of the compound I was suspended by stirring in 1 mL of DMF at 40° C. for 72 h, and then centrifuged. The solid was washed with n-heptane and then dried to provide the crystal form II of the compound I. An XRPD pattern of the resulting crystal form II is as shown in FIG. 22, and XRPD peak positions and relative peak intensities are provided in Table 10. A DSC pattern is as shown in FIG. 23. As can be seen from a TGA pattern shown in FIG. 24, when a sample was heated to 160° C., the weight loss was 13.6%.

TABLE 10

XRPD Data of Crystal Form II of Compound I

| Peak position 2θ (°) ± 0.2° | Relative peak intensity % |
|---|---|
| 6.48 | 8.35 |
| 9.75 | 17.06 |
| 10.82 | 18.82 |
| 12.69 | 22.14 |
| 15.03 | 58.21 |
| 15.31 | 20.01 |
| 15.50 | 6.18 |
| 15.78 | 32.56 |
| 16.25 | 44.53 |
| 18.54 | 25.2 |
| 18.90 | 15.9 |
| 19.27 | 7.49 |
| 19.39 | 9.14 |
| 19.62 | 22.81 |
| 20.18 | 25.76 |
| 20.43 | 15.06 |
| 20.61 | 85.7 |
| 21.25 | 33.05 |
| 21.69 | 34.17 |
| 22.04 | 16.44 |
| 22.61 | 100 |
| 23.60 | 12.84 |
| 23.93 | 13.32 |
| 25.65 | 26.94 |
| 26.48 | 5.59 |
| 27.70 | 8.54 |
| 27.96 | 9.56 |
| 29.76 | 8.93 |
| 32.17 | 19.91 |
| 20.43 | 15.06 |

Example 13: Preparation of Crystal Form III of Compound I

An amorphous form (about 100 mg) of the compound I was suspended by stirring in 1 mL of n-propanol at 20° C. for 72 h, then centrifuged, and dried to provide the crystal form III of the compound I. An XRPD pattern of the resulting crystal form III is as shown in FIG. 25, and XRPD peak positions and relative peak intensities are provided in Table 11. A DSC pattern is as shown in FIG. 26. As can be seen from a TGA pattern shown in FIG. 27, when a sample was heated to 160° C., the weight loss was 10.4%.

TABLE 11

XRPD Data of Crystal Form III of Compound I

| Peak position 2θ (°) ± 0.2° | Relative peak intensity % |
|---|---|
| 8.29 | 8.94 |
| 9.06 | 81.05 |
| 9.95 | 40.75 |
| 12.34 | 43.97 |
| 12.68 | 19.39 |
| 14.30 | 39.42 |
| 14.81 | 8.45 |
| 15.57 | 92.39 |
| 16.00 | 38.25 |
| 17.29 | 19.37 |
| 17.71 | 18.41 |
| 18.55 | 25.2 |
| 18.87 | 9.22 |

TABLE 11-continued

| XRPD Data of Crystal Form III of Compound I | |
|---|---|
| Peak position 2θ (°) ± 0.2° | Relative peak intensity % |
| 20.05 | 26.98 |
| 20.29 | 54.69 |
| 20.70 | 10.04 |
| 20.96 | 13.14 |
| 22.01 | 80.29 |
| 23.62 | 35.28 |
| 25.21 | 100 |
| 25.54 | 6.14 |
| 27.38 | 30.78 |
| 28.15 | 12.91 |
| 32.25 | 6.87 |
| 33.86 | 9.03 |

Example 14: Preparation of Crystal Form IV of Compound I

An amorphous form (about 100 mg) of the compound 1 was suspended by stirring in 1 mL of dichloromethane at 20° C. for 72 h, then centrifuged, and dried to provide the crystal form IV of the compound 1. An XRPD pattern of the resulting crystal form IV is as shown in FIG. 28, and XRPD peak positions and relative peak intensities are provided in Table 12. A DSC pattern is as shown in FIG. 29. As can be seen from a TGA pattern shown in FIG. 30, when a sample was heated to 220° C., the weight loss was about 4%.

TABLE 12

| XRPD Data of Crystal Form IV of Compound I | |
|---|---|
| Peak position 2θ (°) ± 0.2° | Relative peak intensity % |
| 7.37 | 8.11 |
| 10.54 | 8.46 |
| 14.86 | 100 |
| 15.04 | 42.2 |
| 15.89 | 11.04 |
| 16.23 | 5.01 |
| 16.70 | 29.65 |
| 18.57 | 29.6 |
| 19.15 | 6.2 |
| 19.54 | 55.98 |
| 20.52 | 6.87 |
| 21.46 | 5.46 |
| 21.84 | 13.05 |
| 22.04 | 10.38 |
| 23.02 | 28.06 |
| 23.54 | 24.95 |
| 23.79 | 33.3 |
| 24.48 | 18.71 |
| 24.96 | 7.79 |
| 25.33 | 24.98 |
| 27.12 | 17.64 |
| 28.61 | 12.19 |
| 33.28 | 5.71 |

Example 15: Preparation of Crystal Form V of Compound I

An amorphous form (about 100 mg) of the compound I was suspended by stirring in 1 mL of acetonitrile at 20° C. for 72 h, then centrifuged, and dried to provide the crystal form V of the compound 1. An XRPD pattern of the resulting crystal form V is as shown in FIG. 31, and XRPD peak positions and relative peak intensities are provided in Table 13. A DSC pattern is as shown in FIG. 32. As can be seen from a TGA pattern shown in FIG. 33, when a sample was heated to 80° C., the weight loss was about 5%.

TABLE 13

| XRPD Data of Crystal Form V of Compound I | |
|---|---|
| Peak position 2θ (°) ± 0.2° | Relative peak intensity % |
| 9.65 | 11.2 |
| 10.69 | 27.56 |
| 11.88 | 13.42 |
| 12.65 | 16.4 |
| 13.75 | 37.46 |
| 14.98 | 24.62 |
| 16.24 | 54.8 |
| 16.52 | 21.54 |
| 18.08 | 57.8 |
| 18.69 | 22.1 |
| 19.07 | 36.14 |
| 19.47 | 13.42 |
| 19.67 | 19.06 |
| 21.49 | 77.93 |
| 22.48 | 30.27 |
| 22.89 | 100 |
| 25.76 | 22.22 |
| 27.31 | 49.18 |
| 27.81 | 23.81 |
| 32.17 | 7.64 |

Example 16: Preparation of Crystal Form VI of Compound I

An amorphous form (about 100 mg) of the compound 1 was dissolved in 1 mg of anhydrous methanol, and the solution was slowly volatilized to provide the crystal form VI of the compound I. An XRPD pattern of the resulting crystal form VI is as shown in FIG. 34, and XRPD peak positions and relative peak intensities are provided in Table 14. A DSC pattern is as shown in FIG. 35, and an onset temperature of an endothermic peak of a sample is about 199.5° C. A TGA pattern is as shown in FIG. 36, and a sample almost had no weight loss before melting, indicating that the crystal form VI is an anhydrous crystal form.

TABLE 14

| XRPD Data of Crystal Form VI of Compound I | |
|---|---|
| Peak position 2θ (°) ± 0.2° | Relative peak intensity % |
| 5.53 | 22.41 |
| 11.17 | 9.3 |
| 12.95 | 10.7 |
| 14.14 | 20.58 |
| 14.88 | 26.54 |
| 15.91 | 43.41 |
| 16.90 | 29.84 |
| 17.16 | 7.41 |
| 17.53 | 11.36 |
| 18.04 | 28.13 |
| 18.70 | 8.74 |
| 19.56 | 100 |
| 20.37 | 36.58 |
| 20.89 | 9.8 |
| 22.63 | 83.87 |
| 23.33 | 5.86 |
| 24.48 | 9.47 |
| 25.15 | 13.08 |
| 26.21 | 17.4 |
| 26.93 | 12.2 |
| 27.24 | 37.66 |

TABLE 14-continued

| XRPD Data of Crystal Form VI of Compound I | |
|---|---|
| Peak position 2θ (°) ± 0.2° | Relative peak intensity % |
| 27.81 | 10.02 |
| 36.21 | 6.82 |

Example 17: Preparation of Crystal Form C of Fumarate Salt of Compound I A crystal form A (6 g) of the fumarate salt of the compound I was added into a glass bottle. 30 mL of ethanol and 30 mL of water were added. The mixture was stirred at 45° C. for 12 h, and then filtered to provide the crystal form C of the fumarate salt of the compound 1. An XRPD pattern of the resulting crystal form C is as shown in FIG. 38, and XRPD peak positions and relative peak intensities are provided in Table 15. A DSC pattern is as shown in FIG. 39. As can be seen from a TGA pattern shown in FIG. 40, when a sample was heated to 100° C., the weight loss was about 7%.

TABLE 15

| XRPD Data of Crystal Form C of Fumarate Salt of Compound I | |
|---|---|
| Peak position 2θ (°) ± 0.2° | Relative peak intensity % |
| 8.52 | 9.32 |
| 9.11 | 100 |
| 10.03 | 10.3 |
| 10.99 | 24.47 |
| 13.22 | 8.84 |
| 13.67 | 6.26 |
| 14.38 | 14.17 |
| 17.00 | 12.68 |
| 17.16 | 13.7 |
| 17.53 | 16.66 |
| 17.93 | 12.33 |
| 18.08 | 14.39 |
| 20.00 | 22.43 |
| 20.21 | 14.08 |
| 20.47 | 5.61 |
| 20.98 | 5.43 |
| 22.28 | 41.41 |
| 23.09 | 8.49 |
| 24.92 | 5.5 |
| 25.08 | 8.81 |
| 25.88 | 93.23 |
| 27.72 | 29.48 |
| 30.72 | 6.43 |
| 36.21 | 6.82 |

Experimental Example 1: Solubility Determination of Crystal Form A of Fumarate Salt of Compound I Solubility data of the crystal form A of the fumarate salt of the compound I at different pH is provided in Table 16.

TABLE 16

| Solubility of Crystal Form A of Fumarate Salt of Compound I at Different pH | |
|---|---|
| Buffer pH | Solubility mg/ml |
| 1.0 | ≥12.2 |
| 2.0 | 3.5 |
| 3.0 | 2.5 |

Experimental Example 2: Stability Experiment of Crystal Form A of Fumarate Salt of Compound I Stability data of the crystal form A of the fumarate salt of the compound I under conditions of influencing factors is provided in Table 17 (HPLC purity is area normalized purity).

TABLE 17

Stability Experiment of Crystal Form A of Fumarate Salt of Compound I

| Conditions | Time | Appearance | Crystal form | HPLC purity |
|---|---|---|---|---|
| Day 0 | | White solid | Crystal form A | 99.6% |
| High temperature 60° C. ± 2° C. | Day 30 | White solid | Crystal form A | 99.3% |
| High humidity 25° C. ± 2° C./92.5% RH ± 5% RH | Day 30 | White solid | Crystal form A | 99.5% |

The experimental results show that the crystal form A of the compound I has goo stability under high temperature/high humidity conditions.

Experimental Example 3: Dynamic Water Adsorption Experiment of Crystal Form A of Fumarate Salt of Compound I Device information: SMS (Surface Measurement Systems) Intrinsic Experimental method: temperature: 25° C.; protective gas $N_2$; maximum equilibration time: 120 min; RH range: 0%-90%-0%.

Figure 41:
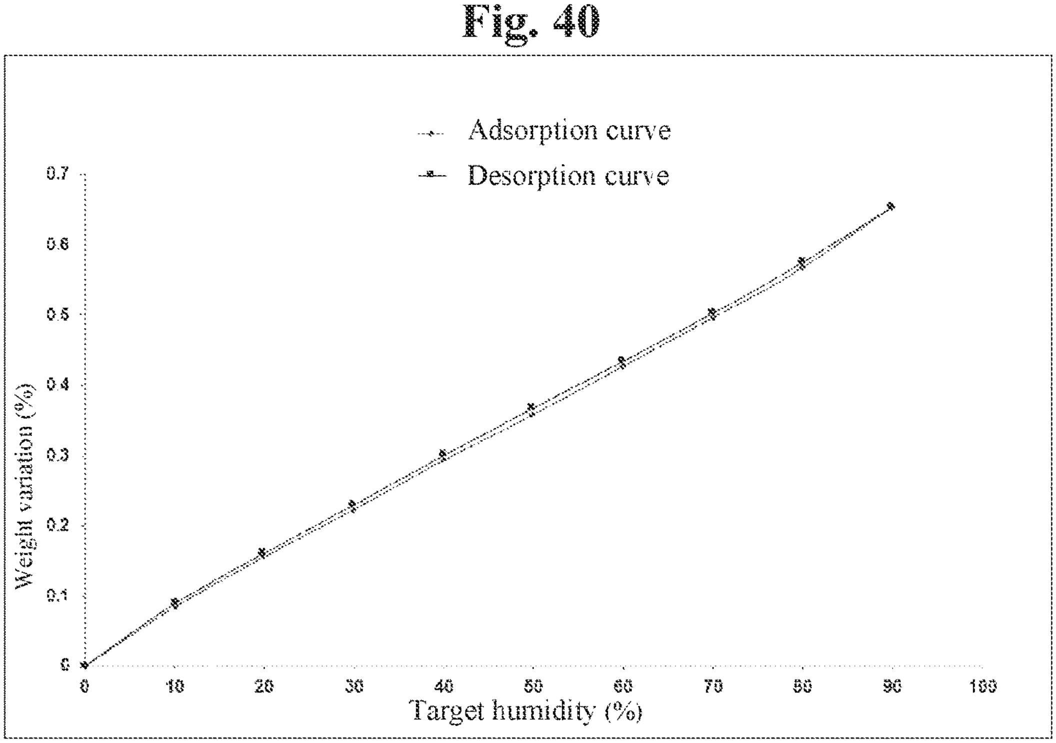
FIG. 41 shows a DVS pattern of a crystal form A of the fumarate salt of the compound I prepared in Example 7.

A DVS pattern of the crystal form A of the fumarate salt of the compound I is as shown in FIG. 41. When the humidity was increased to 90%, the crystal form A of the fumarate salt of the compound I absorbed about 0.7% water, and when the humidity was decreased from 90% to 0%, the adsorbed water can be fully desorbed. The crystal form remained changed before and after the DVS test.

Experimental Example 4: Dynamic Water Adsorption Experiment of Crystal Form VI of Compound 1

Device information: SMS (Surface Measurement Systems) Intrinsic

Experimental method: temperature: 25° C.; protective gas $N_2$; maximum equilibration time: 120 min; RH range: 0%-90%-0%.

Figure 42:
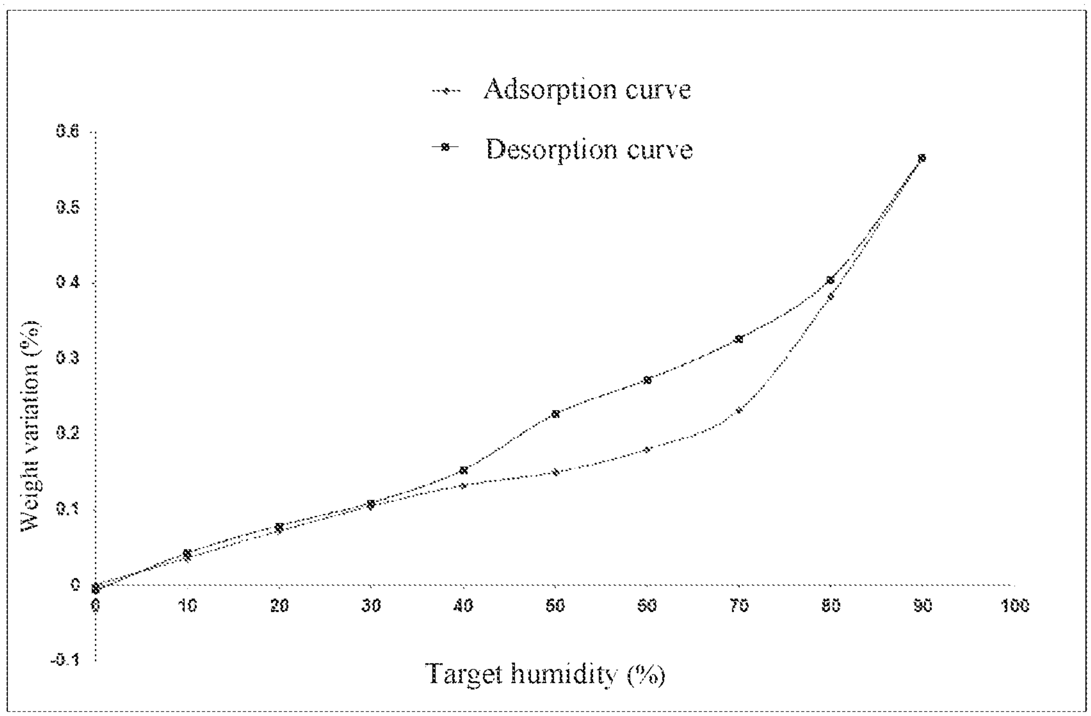
FIG. 42 shows a DVS pattern of the crystal form VI of the compound I prepared in Example 16.

A DVS pattern of the crystal form VI of the compound I is as shown in FIG. 42. When the humidity was increased to 90%, the crystal form VI of the compound I absorbed about 0.6% water, and when the humidity was decreased from 90% to 0%, the adsorbed water can be fully desorbed. The crystal form remained changed before and after the DVS test.

Experimental Example 5: Inhibitory Effects of Crystal Form A of Fumarate Salt of Compound I on RET Enzymes The inhibitory effects of the crystal form A of the fumarate salt of the compound I on the activity of wild-type RET, mutant-type RET ($RET^{V804M}$ $RET^{V804L}$, and $RET^{M918T}$), and fusion-type RET (CCDC6-RET and KIF5B-RET) were determined using HTRF KinEASE-TK (Cisbio) kit.

After pre-incubation of the above different types of RET enzymes and different concentrations of the test compounds (9 concentration points) at room temperature for 30 min, a substrate and adenosine triphosphate (ATP) were added to initiate the reaction. After incubation at room temperature for 40 min, TK antibody-cryptate and streptavidin-XL665 were added, and after incubation at room temperature for 60 min, the detection was performed. The reaction conditions for the different types of RET enzymes are shown in the table below:

| RET enzyme type | RET (nM) | ATP (μM) | TK-substrate (μM) |
|---|---|---|---|
| RET | 0.2 | 30 | 1 |
| $RET^{V804M}$ | 0.6 | 15 | 1 |
| $RET^{V804L}$ | 0.6 | 10 | 1 |
| $RET^{M918T}$ | 0.3 | 15 | 1 |
| CCDC6-RET | 0.3 | 15 | 1 |
| KIF5B-RET | 0.6 | 25 | 1 |

With the solvent group (DMSO) as the negative control and the buffer group (without RET enzyme) as the blank control, the relative inhibitory activity percentages of the compound at different concentrations were computed as per the following equation:

Relative inhibitory activity percentage=1−(compound group of different concentrations-blank control)/(negative control-blank control)*100%

The relative inhibitory activity percentages of the compound at different concentrations were plotted with respect to the compound concentrations, and the curve was fitted in accordance with a four-parameter model to compute the $IC_{50}$ value as per the following equation:

$y$=min+(max−min)/(1+($x$/$IC_{50}$)^(−Hillslope))

where y is the relative inhibitory activity percentage, max and min are a maximum value of the fitted curve, and a minimum value of the fitted curve respectively, x is a logarithmic concentration of the compound, and Hillslope is a slope of the curve.

The inhibitory effects of the crystal form A of the fumarate salt of the compound I in the present invention on the wild-type RET enzyme, the $RET^{V804M}$ enzyme, the $RET^{V804L}$ enzyme, the $RET^{M918T}$ enzyme, the CCDC6-RET enzyme, and the KIF5B-RET enzyme are as shown in the following table.

Inhibitory $IC_{50}$ Values of Crystal Form A of Fumarate Salt of Compound I on Various Types of RET Enzymes

| RET enzyme type | Inhibitory $IC_{50}$ (nM) on RET enzyme |
|---|---|
| RET | 0.56 ± 0.09 |
| $RET^{V804M}$ | 0.60 ± 0.20 |
| $RET^{V804L}$ | 1.59 ± 0.51 |
| $RET^{M918T}$ | 2.23 ± 0.64 |
| CCDC6-RET | 2.48 ± 1.00 |
| KIF5B-RET | 0.56 ± 0.10 |

The data in the above table shows that the crystal form A of the fumarate salt of the compound I has obvious inhibitory effects on enzymatic activities of the 6 tested types of RET kinases (RET, $RET^{V804M}$, $RET^{V804L}$, $RET^{M918T}$ CCDC6-RET, and KIF5B-RET).

Experimental Example 6: Pharmacokinetic Study on Crystal Form A of Fumarate Salt of Compound I in Mice Female Balb/c mice (6 mice) were orally administered with 1 mg/kg of the crystal form A of the fumarate salt of the compound I by gavage. The compound was first dissolved with 0.5% methylcellulose solution and ultrasonicated to ensure complete dissolution or uniform suspension of the compound. 30 min, 1 h, 2 h, 4 h, 8 h, 12 h, 16 h, and 24 h after administration, 0.2 mL of blood (EDTA-$K_2$ anticoagulated) was venously collected. The collected whole blood was temporarily stored in an ice box, and centrifuged for 10 min within 2 h to separate the plasma (4° C.). The collected plasma was stored in a refrigerator at −80° C. prior to testing.

The blood concentration of the compound I was detected by LC-MS/MS, and the linear range was from 10 to 10000 ng/mL. The computed pharmacokinetic parameters are as shown in the table below.

Pharmacokinetic Study on Crystal Form A of Fumarate Salt of Compound I in Mice

| Parameters | Unit | PO (1 mg/kg) |
|---|---|---|
| $AUC_{INF}$ | h*ng/ml | 11381 |
| AUClast | h*ng/ml | 11354 |
| $C_{max}$ | ng/ml | 2060 |
| Vd | ml/kg | 356 |
| Cl | ml/h/kg | 88 |
| $t_{1/2}$ | h | 2.81 |
| $T_{max}$ | h | 1.00 |

The data in the above table shows that the crystal form A of the fumarate salt of the compound I has excellent pharmacokinetic properties in mice.

The present invention is further described in detail in the above specific embodiments. However, it should be understood that the scope of the above subject matter of the present invention is not merely limited to the listed Examples, and the technical solutions implemented based on the content of the present invention fall within the scope of the present invention.

The invention claimed is:

1. A salt of compound I:

I

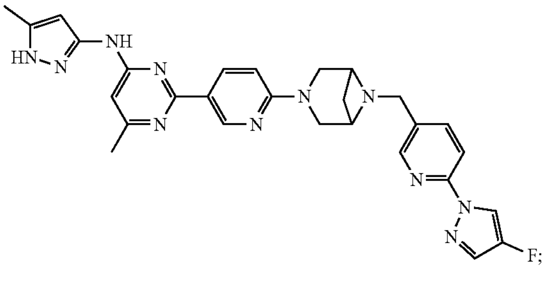

wherein the salt is a fumarate salt; wherein the salt of compound I has a molar ratio of 1:1 of compound I to fumaric acid; and wherein the salt is selected from:

a crystal form A, characterized in that an XRPD pattern of the crystal form A comprises diffraction peaks at 2θ of about 5.44±0.2°, 9.75±0.2°, and/or 18.43±0.2°;

a crystal form B, characterized in that an XRPD pattern of the crystal form B comprises diffraction peaks at 2θ of about 9.12±0.2°, 16.57±0.2°, 24.78±0.2°, and/or 25.74±0.2°;

a crystal form C, characterized in that an XRPD pattern of the crystal form C comprises diffraction peaks at 2θ of about 9.13±0.2° and/or 26.08±0.2°;

a crystal form D, characterized in that an XRPD pattern of the crystal form D is substantially as shown in FIG. 13;

a crystal form F, characterized in that an XRPD pattern of the crystal form Fis substantially as shown in FIG. 16; and a crystal form G, characterized in that an XRPD pattern of the crystal form G is substantially as shown in FIG. 19.

2. The salt of claim 1, being a crystal form B, characterized in that an XRPD pattern of the crystal form B comprises diffraction peaks at 2θ of about 9.12±0.2°, 16.57±0.2°, 24.78±0.2°, and/or 25.74±0.2°.

3. The salt of claim 1, being a crystal form C, characterized in that an XRPD pattern of the crystal form C comprises diffraction peaks at 2θ of about 9.13±0.2° and/or 26.08±0.2°.

4. The salt of claim 1, selected from:

a crystal form D, characterized in that an XRPD pattern of the crystal form D is substantially as shown in FIG. 13;

a crystal form F, characterized in that an XRPD pattern of the crystal form Fis substantially as shown in FIG. 16; and a crystal form G, characterized in that an XRPD pattern of the crystal form G is substantially as shown in FIG. 19.

5. A salt of compound I:

I

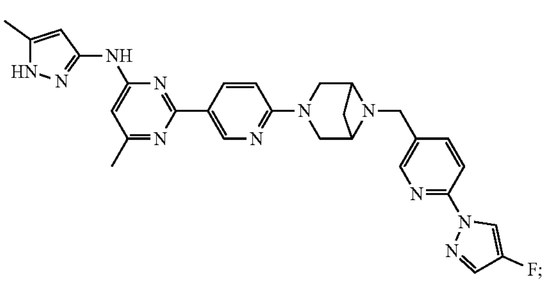

;

wherein the salt is a p-toluenesulfonate salt, the salt being a crystal form A, characterized in that an XRPD pattern of the crystal form A comprises diffraction peaks at 2θ of about 4.69±0.2° and/or 13.87±0.2°.

6. A crystalline form of compound I:

I

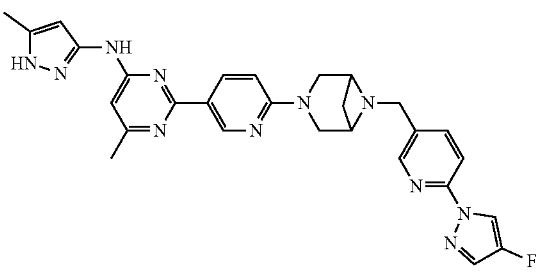

wherein the crystalline form is selected from:

form I, wherein an XRPD pattern of the crystal form I comprises diffraction peaks at 2θ of about 18.00±0.2°, 19.55±0.2°, 22.62±0.2°, and 27.20±0.2°;

form II, wherein an XRPD pattern of the crystal form II comprises diffraction peaks at 2θ of about 15.03±0.2°, 16.25±0.2°, 20.61±0.2°, 21.69±0.2°, and 22.61±0.2°;

form III, wherein an XRPD pattern of the crystal form III is substantially as shown in FIG. 25;

form IV, wherein an XRPD pattern of the crystal form IV is substantially as shown in FIG. 28;

form V, wherein an XRPD pattern of the crystal form V is substantially as shown in FIG. 31; and form VI, wherein an XRPD pattern of the crystal form VI comprises diffraction peaks at 2θ of about 18.04±0.2°, 19.56±0.2°, 22.63±0.2°, and 27.24±0.2°.

7. A pharmaceutical composition comprising the salt of claim 1, and one or more pharmaceutically acceptable carriers.

8. A pharmaceutical composition comprising the salt of claim 5, and one or more pharmaceutically acceptable carriers.

9. A pharmaceutical composition comprising the crystalline form of compound I according to claim 6, and one or more pharmaceutically acceptable carriers.

10. A method for preventing or treating a disease or condition associated with RET activity, comprising administering to an individual in need thereof a therapeutically effective amount of the salt of claim 1.

11. A method for preventing or treating a disease or condition associated with RET activity, comprising administering to an individual in need thereof a therapeutically effective amount of the salt of claim 5.

12. A method for preventing or treating a disease or condition associated with RET activity, comprising administering to an individual in need thereof a therapeutically effective amount of the compound of claim 6.

13. The method of claim 10, wherein the disease or condition associated with RET activity is selected from irritable bowel syndrome and a cancer or tumor.

14. The method of claim 13, wherein the cancer is selected from lung cancer, breast cancer, head and neck cancer, rectal cancer, liver cancer, lymphoma, thyroid cancer, colon cancer, multiple myeloma, melanoma, glioma, brain tumor, and sarcoma.

15. The salt of claim 1, being a crystal form A, characterized in that an XRPD pattern of the crystal form A comprises diffraction peaks at 2θ of about 5.44±0.2°, 9.75±0.2°, and/or 18.43±0.2°.

16. The crystalline form of claim 6, wherein the crystalline form is a crystal form VI, characterized in that the XRPD pattern of the crystal form VI is substantially as shown in FIG. 34.

17. The method of claim 14, wherein the lung cancer is non small cell lung cancer.

18. The method of claim 14, wherein the thyroid cancer is medullary thyroid cancer or papillary thyroid cancer.

19. The salt of claim 1, being a crystal form A, characterized in that an XRPD pattern of the crystal form A further comprises diffraction peaks at 2θ of about 17.28±0.2°, 18.13±0.2°, 26.55±0.2°, and/or 27.86±0.2°.

20. The salt of claim 1, being a crystal form A, characterized in that an XRPD pattern of the crystal form A further comprises diffraction peaks at 2θ of about 10.99±0.2°, 12.09±0.2°, 13.89±0.2°, 14.87±0.2°, 16.25±0.2° and/or 19.11±0.2°.

21. The salt of claim 1, being a crystal form A, characterized in that an XRPD pattern of the crystal form A further comprises diffraction peaks at 2θ of about 15.63±0.2°, 20.48±0.2°, 21.55±0.2°, 22.14±0.2°, 22.55±0.2°, 23.56±0.2°, 23.83±0.2°, and/or 29.86±0.2°.

22. The salt of claim 1, being a crystal form A, characterized in that an XRPD pattern of the crystal form A further comprises diffraction peaks at 2θ of about 12.84±0.2°, 16.56±0.2°, 16.74±0.2°, 17.02±0.2°, 19.70±0.2°, 21.08±0.2°, and/or 25.64±0.2°.

23. The salt of claim 1, being a crystal form A, characterized in that an XRPD pattern of the crystal form A is substantially as shown in FIG. 1 or FIG. 2.

24. The salt of claim 1, being a crystal form A, characterized in that an XRPD pattern of the crystal form A is as shown in FIG. 1 or FIG. 2.

* * * * *